(12) United States Patent
Nagasaki et al.

(10) Patent No.: US 10,155,009 B2
(45) Date of Patent: Dec. 18, 2018

(54) POLYION COMPLEX OF POLY(L-ARGININE) SEGMENT-CONTAINING BLOCK COPOLYMER AND POLYANIONIC POLYMER

(71) Applicant: GENERAL INCORPORATED ASSOCIATION TSUKUBA GLOBAL INNOVATION PROMOTION AGENCY, Ibaraki (JP)

(72) Inventors: Yukio Nagasaki, Ibaraki (JP); Shinpei Kudo, Ibaraki (JP); Yuji Hiramatsu, Ibaraki (JP); Hiroaki Sakamoto, Ibaraki (JP); Quoc Thang Bui, Ibaraki (JP); Binh Long Vong, Ibaraki (JP)

(73) Assignee: GENERAL INCORPORATED ASSOCIATION TSUKUBA GLOBAL INNOVATION PROMOTION AGENCY, Ibaraki (JP)

(*) Notice: Subject to any disclaimer, the term of this patent is extended or adjusted under 35 U.S.C. 154(b) by 0 days.

(21) Appl. No.: 15/566,237

(22) PCT Filed: Apr. 15, 2016

(86) PCT No.: PCT/JP2016/062062
§ 371 (c)(1),
(2) Date: Oct. 13, 2017

(87) PCT Pub. No.: WO2016/167333
PCT Pub. Date: Oct. 20, 2016

(65) Prior Publication Data
US 2018/0085395 A1 Mar. 29, 2018

(30) Foreign Application Priority Data
Apr. 16, 2015 (JP) ................................. 2015-083987

(51) Int. Cl.
| | | |
|---|---|---|
| A61K 31/785 | (2006.01) | |
| A61K 47/10 | (2017.01) | |
| A61K 47/34 | (2017.01) | |
| C08L 71/08 | (2006.01) | |
| C08L 77/04 | (2006.01) | |
| A61K 38/00 | (2006.01) | |
| A61K 47/32 | (2006.01) | |
| A61K 47/36 | (2006.01) | |
| A61K 47/42 | (2017.01) | |

(52) U.S. Cl.
CPC ............ *A61K 31/785* (2013.01); *A61K 38/00* (2013.01); *A61K 47/10* (2013.01); *A61K 47/32* (2013.01); *A61K 47/34* (2013.01); *A61K 47/36* (2013.01); *A61K 47/42* (2013.01); *C08L 71/08* (2013.01); *C08L 77/04* (2013.01); *C08L 2203/02* (2013.01)

(58) Field of Classification Search
CPC ...... A61K 38/00; A61K 31/785; A61K 47/10; A61K 47/32; A61K 47/34; A61K 47/36; A61K 47/42; C08L 71/08; C08L 77/04; C08L 2203/02
See application file for complete search history.

(56) References Cited

U.S. PATENT DOCUMENTS

| | | | |
|---|---|---|---|
| 2003/0147958 A1* | 8/2003 | Ahn ...................... | A61K 47/34 424/486 |
| 2004/0097467 A1 | 5/2004 | Juturu et al. | |
| 2010/0061953 A1 | 3/2010 | Luengo et al. | |
| 2010/0092416 A1 | 4/2010 | Luengo et al. | |
| 2012/0076836 A1* | 3/2012 | Hori et al. | |
| 2014/0356315 A1 | 12/2014 | Nagasaki et al. | |
| 2016/0346438 A1 | 12/2016 | Nagasaki et al. | |

FOREIGN PATENT DOCUMENTS

| | | |
|---|---|---|
| JP | 2006-501224 | 1/2006 |
| WO | 2008/104694 | 9/2008 |
| WO | 2013/111801 | 8/2013 |
| WO | 2015/118993 | 8/2015 |

OTHER PUBLICATIONS

International Search Report dated Jun. 28, 2016 in International (PCT) Application No. PCT/JP2016/062062.
Lubec et al., "Decreased Tumor Incidence and Increased Survival by One Year Oral Low Dose Arginine Supplementation in the Mouse", Life Sciences, 58(25):2317-2325 (1996).
Harada et al., "Formation of Polyion Complex Micelles in an Aqueous Milieu from a pair of Oppositely-Charged Block Copolymers with Poly(ethylene glycol) Segments", Macromolecules, 28:5294-5299 (1995).
Bernatowicz et al., "1H-Pyrazole-1-carboxamidine Hydrochloride: An Attractive Reagent for Guanylation of Amines and Its Application to Peptide Synthesis", Journal of Organic Chemistry, 57:2497-2502 (1992).
Holowka et al., "Polyarginine segments in block copolypeptides drive both vesicular assembly and intracellular delivery", Nature materials, 6:52-57 (2007).

* cited by examiner

*Primary Examiner* — Alma Pipic
(74) *Attorney, Agent, or Firm* — Wenderoth, Lind & Ponack, L.L.P.

(57) ABSTRACT

An object of the present invention is to provide a composition that serves as an efficient arginine substrate for inducible NO synthase (iNOS) in tumor. The present invention provides a polyion complex (PIC) of PEG-b-poly(L-Arg) or poly(L-Arg)-b-PEG-b-poly(L-Arg) and a polyanionic polymer, and use thereof.

3 Claims, 12 Drawing Sheets

[Fig. 1]
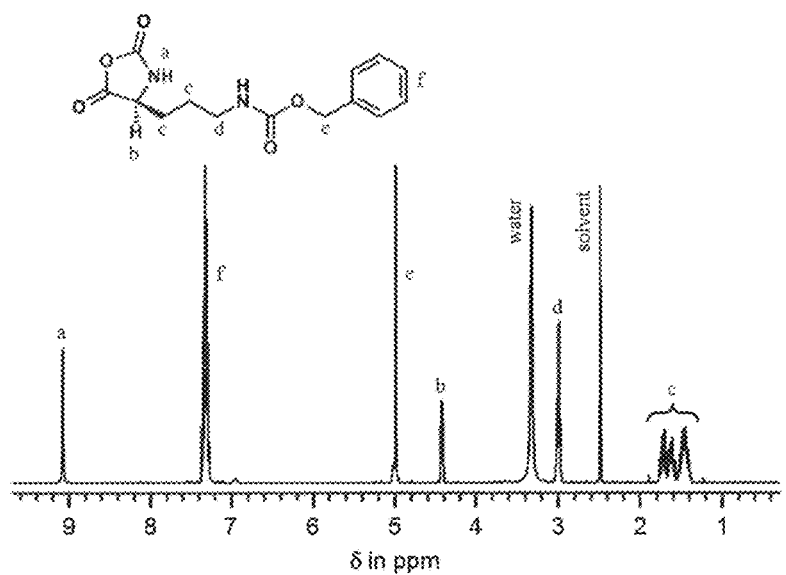
[Fig. 2]
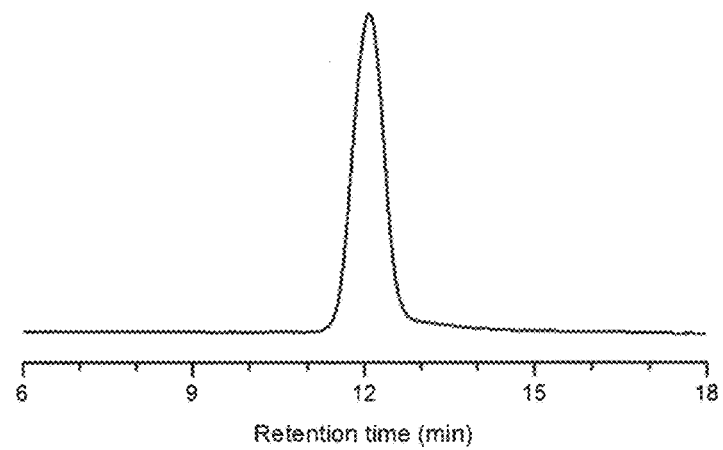

[Fig. 3]
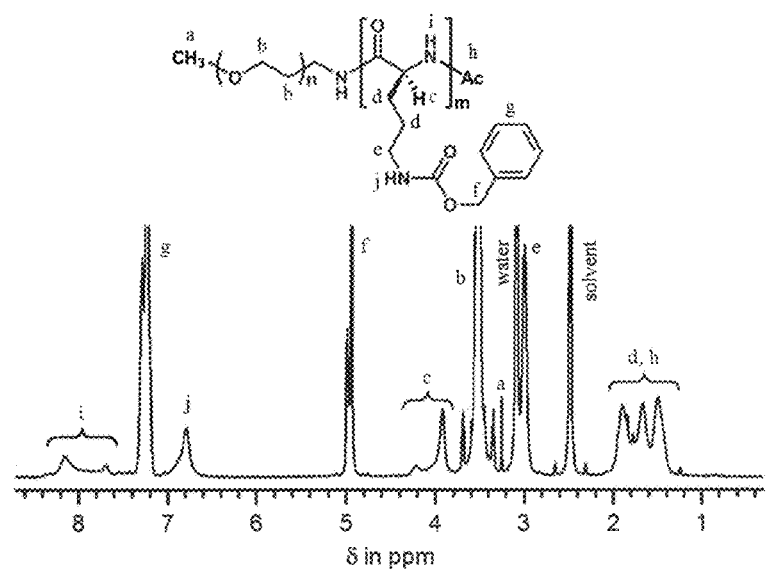
[Fig. 4]
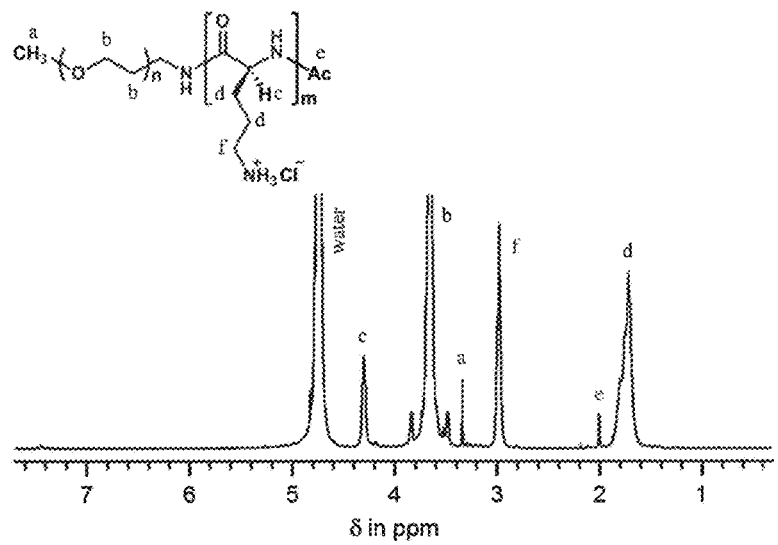

[Fig. 5]
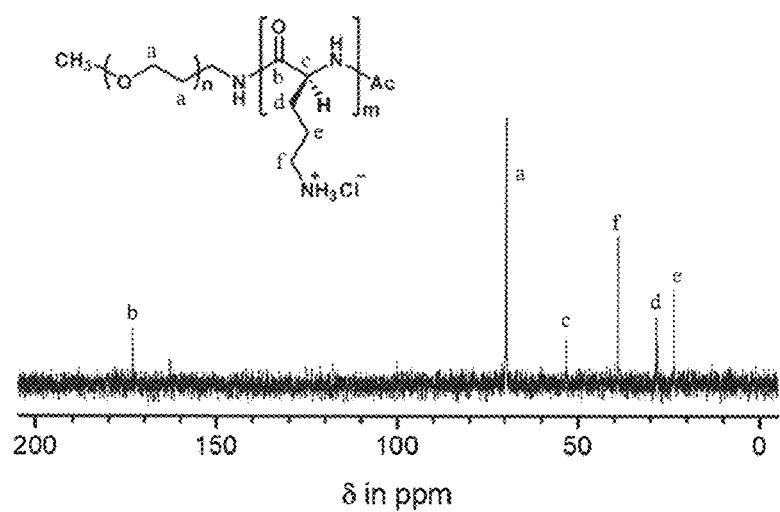
[Fig. 6]
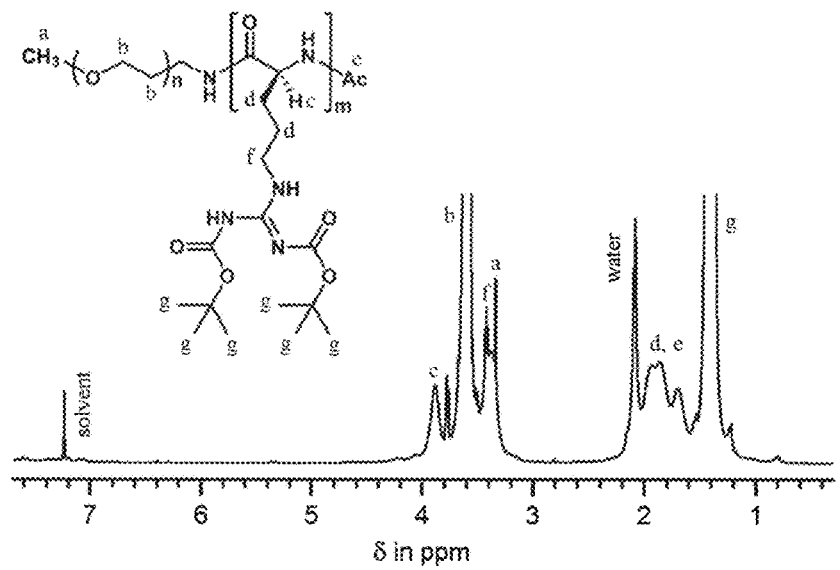

[Fig. 7]
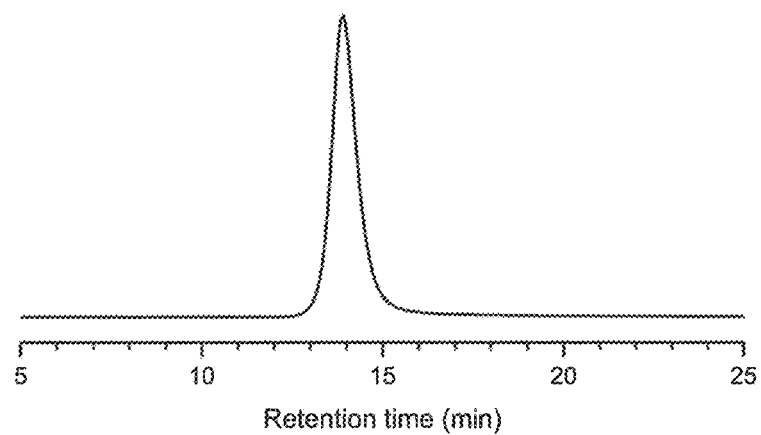
[Fig. 8]
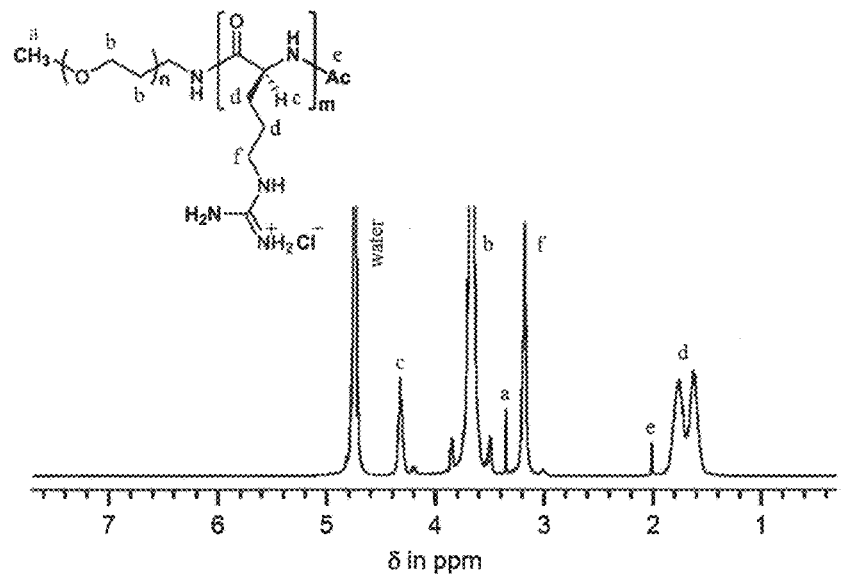

[Fig. 9]
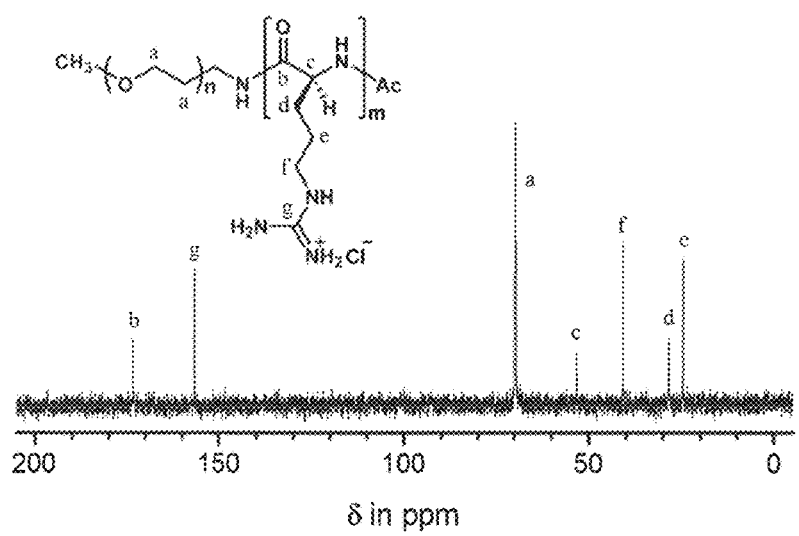
[Fig. 10]
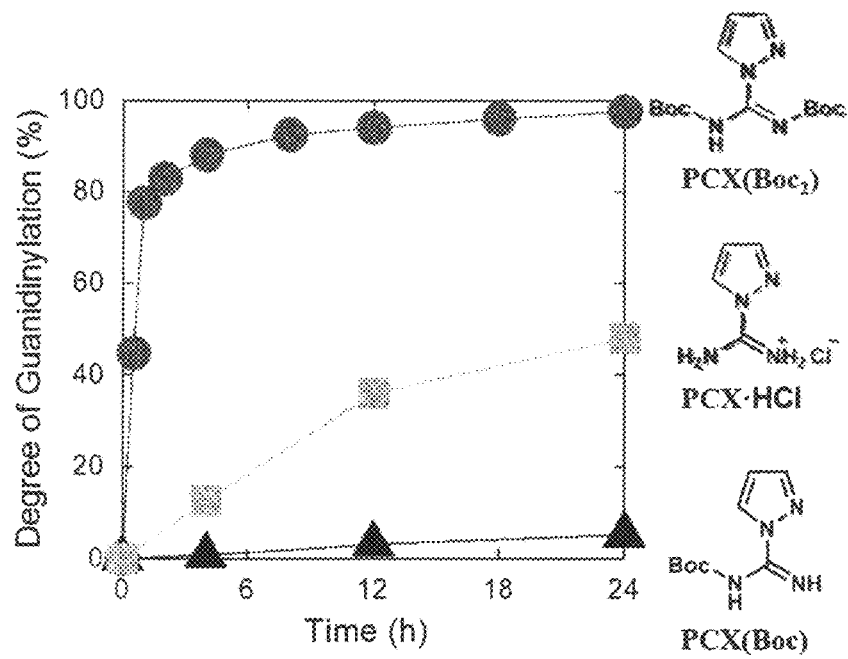

[Fig. 11]
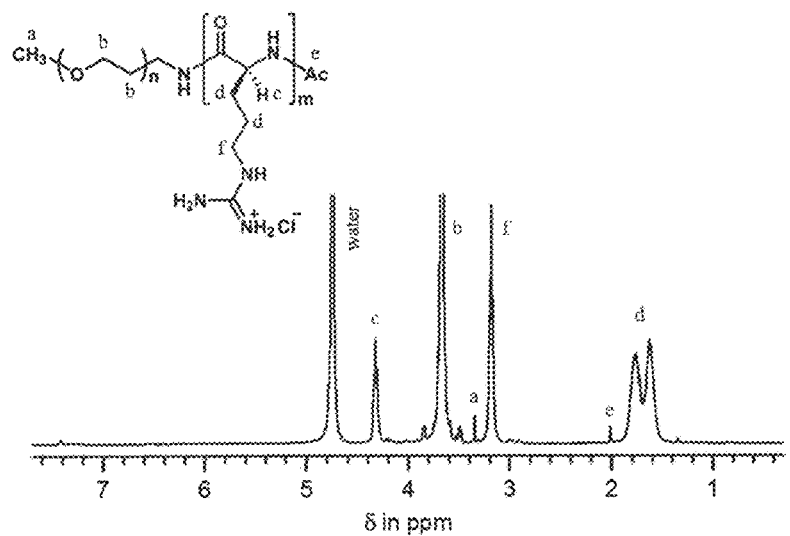
[Fig. 12]
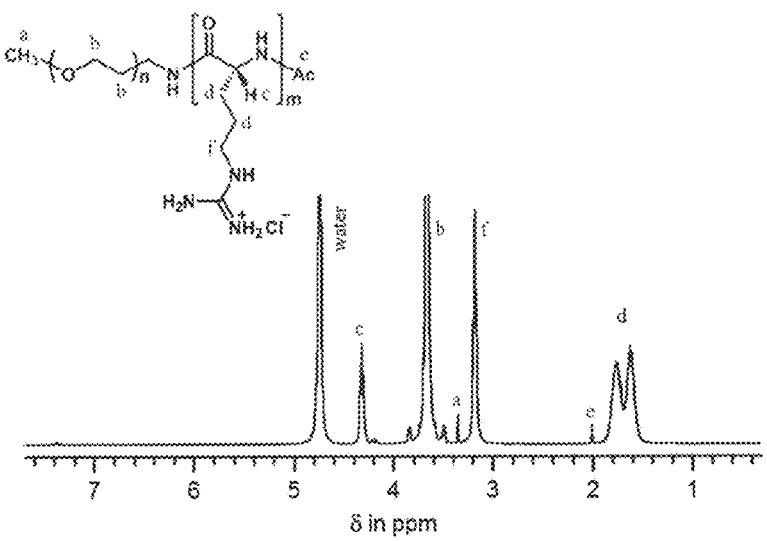

[Fig. 13]
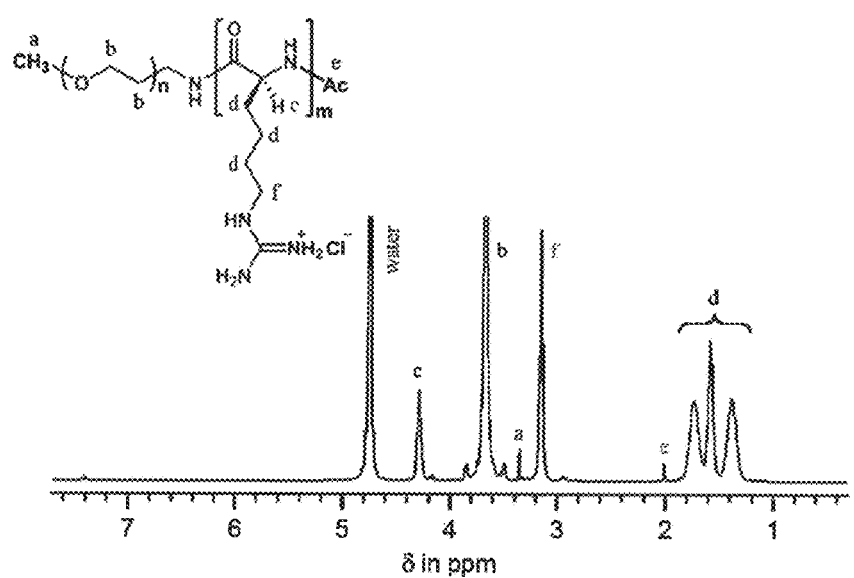

[Fig. 14]
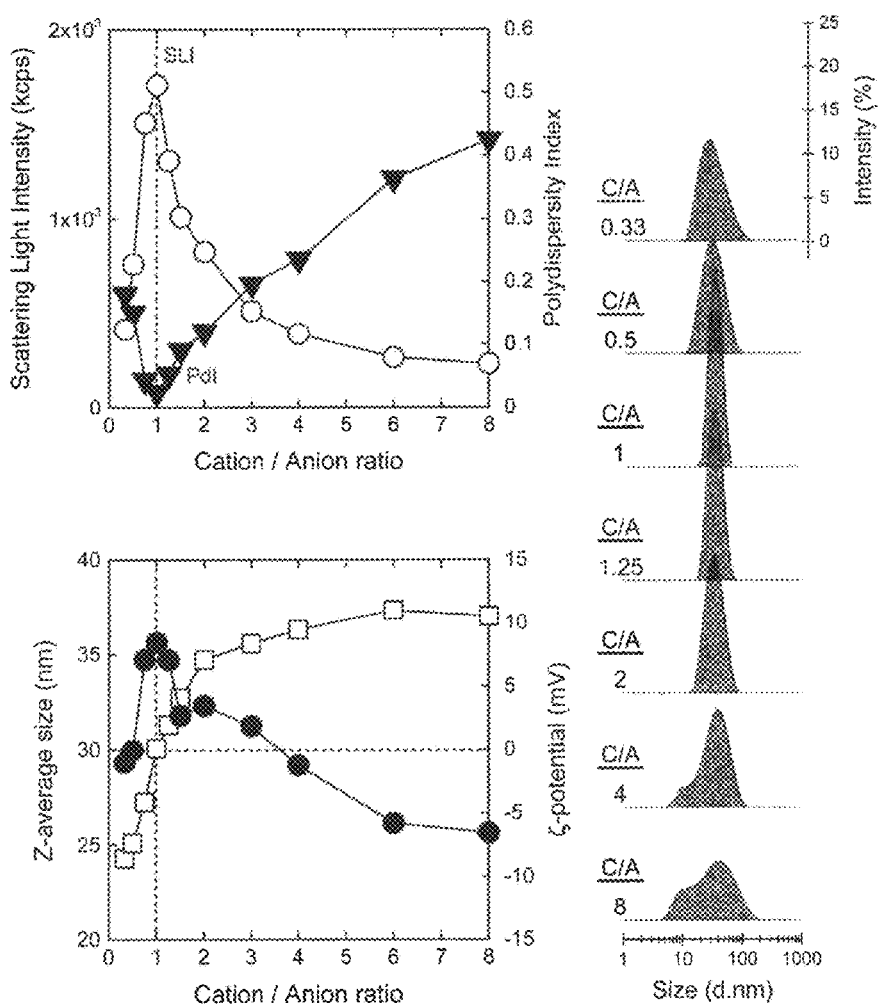

[Fig. 15]
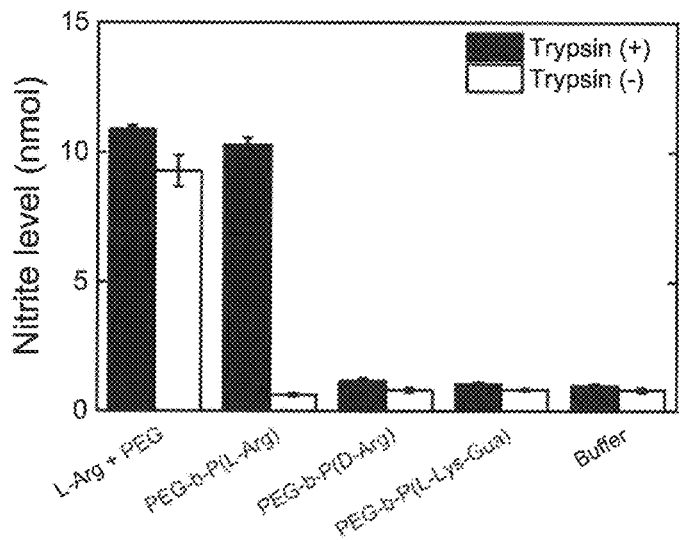
[Fig. 16]
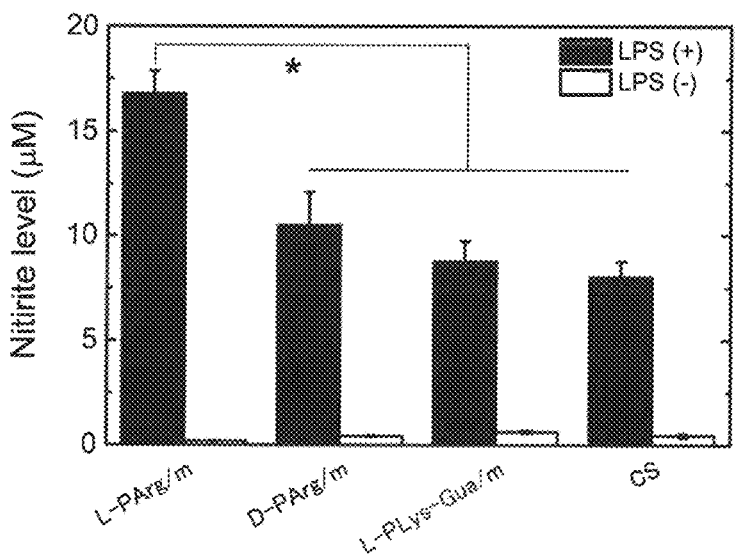

[Fig. 17]
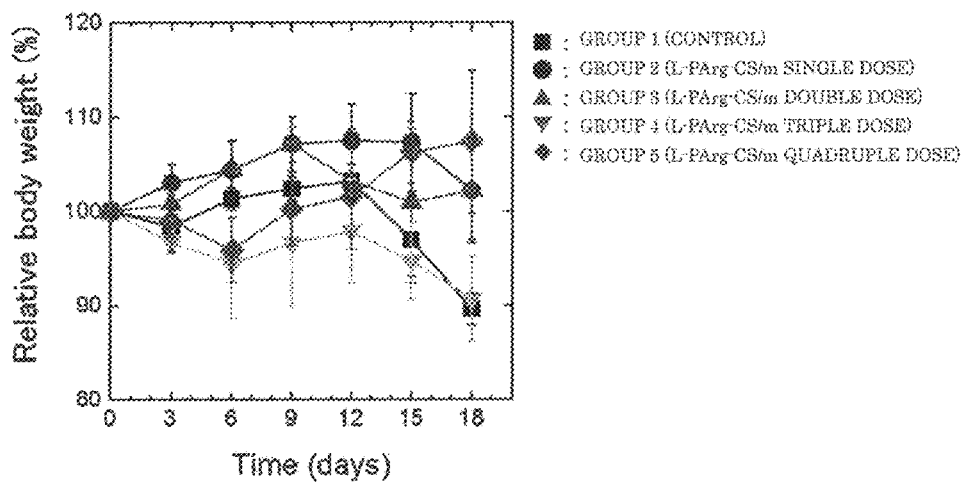
[Fig. 18]
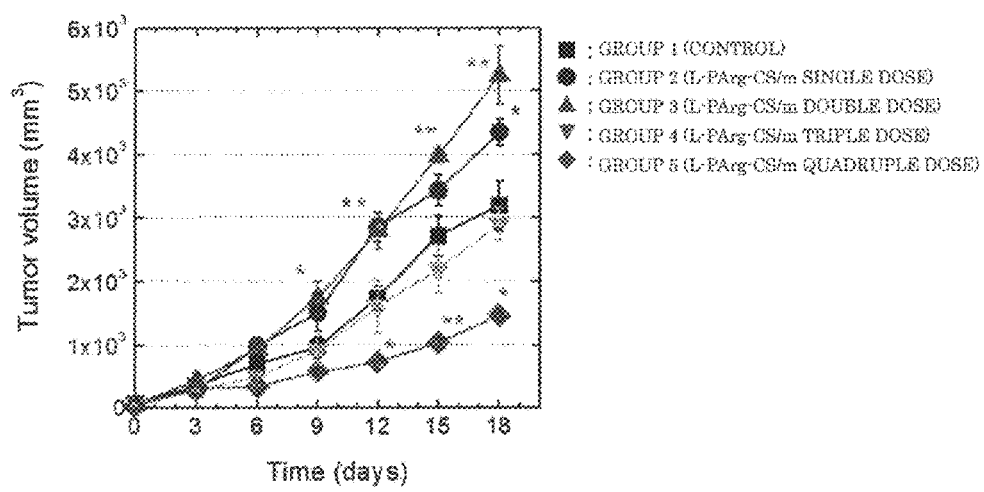

[Fig. 19]
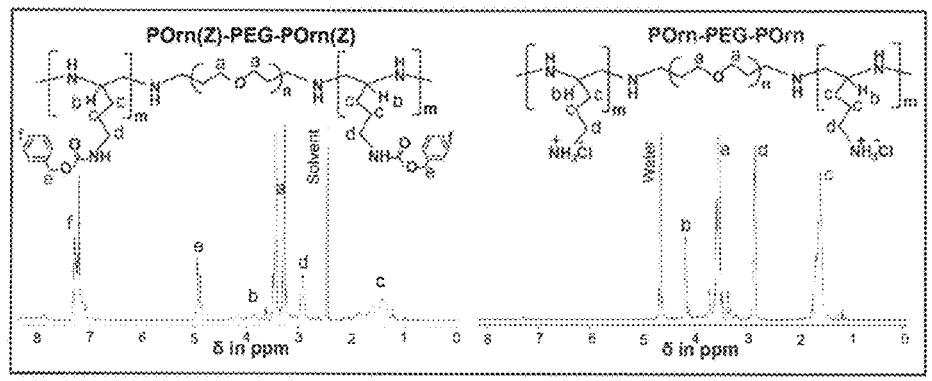
[Fig. 20]
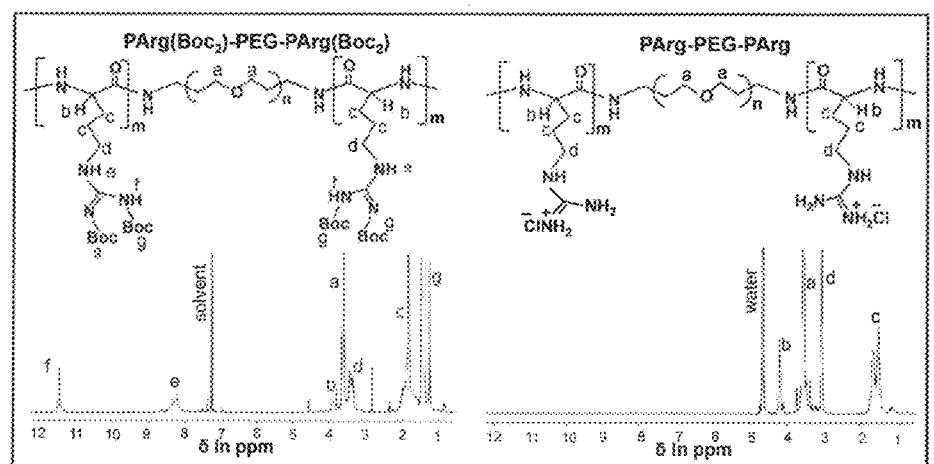
[Fig. 21]
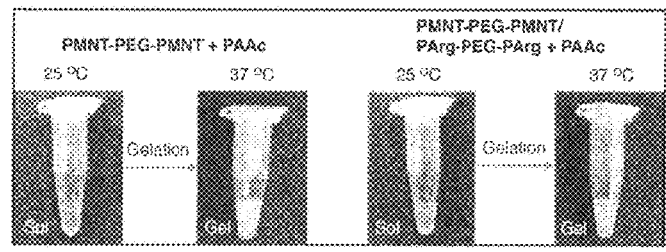

[Fig. 22]
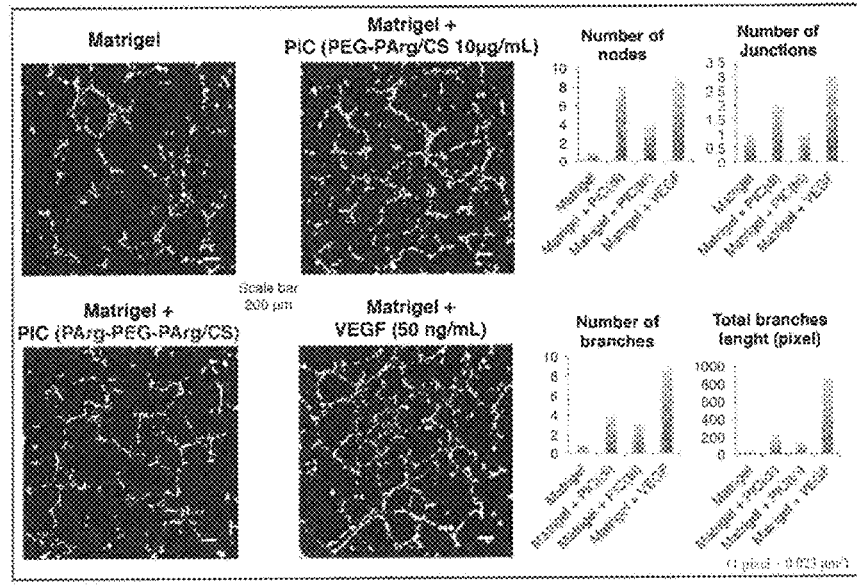
[Fig. 23]
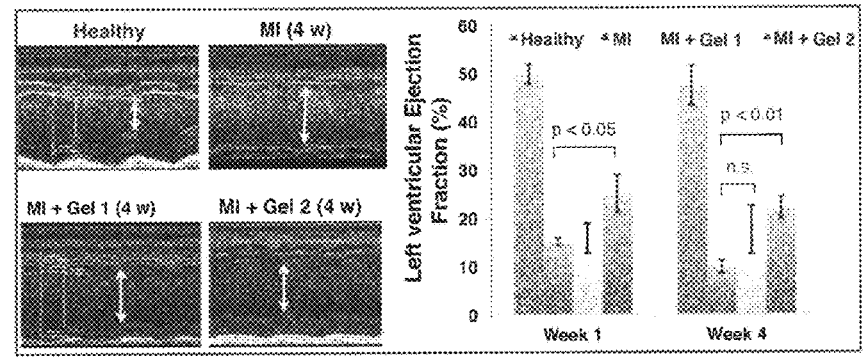
[Fig. 24]
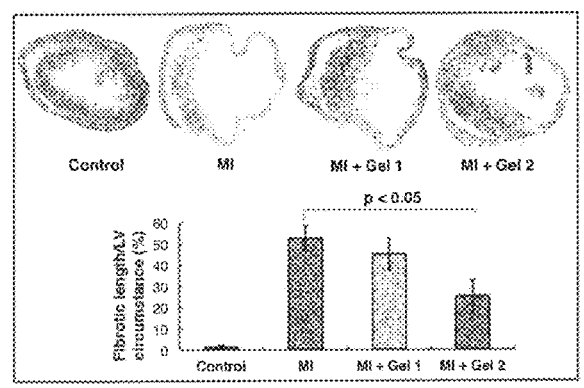

POLYION COMPLEX OF POLY(L-ARGININE) SEGMENT-CONTAINING BLOCK COPOLYMER AND POLYANIONIC POLYMER

TECHNICAL FIELD

The present invention relates to a polyion complex (PIC) containing poly(ethylene glycol)-b-poly(L-arginine) or poly(L-arginine)-b-poly(ethylene glycol)-b-poly(L-arginine) and a polyanionic polymer, application of the PIC such as use thereof for activation of macrophages in tumor tissue, the block copolymer and a method for producing the same.

BACKGROUND ART

Tumor tissue contains not only cancer cells but also many immune cells. At an early stage of tumor tissue formation, growth of tumor tissue is suppressed by anticancer activity of immune cells and cancer cells are eliminated from the body. However, when the anticancer activity of the immune cells is weakened, tumor tissue continues to grow and in some cases metastasis of the tumor tissue may occur. A therapy in which the immune cells in tumor tissue are activated to kill cancer cells is called cancer immunotherapy, which has attracted attention in recent years. In conventional cancer immunotherapy, cytotoxic T cells and natural killer cells are activated by overdose of Interleukin-2 (IL-2). However, tumor tissue does not have a mechanism to specifically take up IL-2 and IL-2 is systemically overdosed under the current situation, and thus significant toxicity has been observed. In addition, there is another problem to be solved in that activation of immune cells is limited under the environment of the tumor in which cancer cells have started secretion of a cytokine called tumor growth factor or transforming growth factor (TGF-β).

SUMMARY OF INVENTION

The inventors of the present invention sought to solve the above problems and focused on activation of a type of immune cells called macrophages. Macrophages abundantly infiltrate into tumor tissues and produce nitric oxide (NO) to induce apoptosis (programmed death) of cancer cells. Activated macrophages express inducible NO synthase (iNOS) intracellularly which generates NO from the substrate, L-arginine. The rate-limiting factor of the enzymatic reaction is the L-arginine concentration and an increased arginine concentration in tumors increases the production rate of NO. Therefore, it is expected that by efficiently delivering L-arginine to tumor tissues, anticancer activity of macrophages may be increased.

Under such circumstances, the inventors of the present invention studied the way to deliver L-arginine by using drug delivery system (DDS) technology in order to efficiently transport L-arginine to tumor tissues.

As a result, the inventors of the present invention synthesized for the first time biodegradable poly(ethylene glycol)-b-poly(L-arginine) [which may be abbreviated as PEG-b-P(L-Arg) or PEG-PArg], and found that nanoparticles of core-shell polyion complex micelles (PIC/m) prepared by electrostatic interaction of the PEG-b-P(L-Arg) with a polyanionic polymer are efficiently accumulated to tumor tissues and, even though the copolymer has L-arginine as a polymeric unit of a poly(L-Arg) segment and the copolymer forms PIC micelles with the polyanionic polymer, the copolymer can be a substrate of iNOS similar to free L-arginine and significantly decreases the tumor volume in experimental mammals having tumors. The inventors of the present invention also found that a triblock copolymer of poly(L-arginine)-b-poly(ethylene glycol)-b-poly(L-arginine) [which may be abbreviated as P(L-Arg)-b-PEG-b-P(L-Arg) or PArg-PEG-PArg] also works in the same manner as the diblock copolymer.

Meanwhile, a prior art document WO2008/104694 discloses a graft amino acid polymer which may encompass PEG-b-P(L-Arg) in general and Japanese Patent Application Publication No. 2006-56864 may disclose a copolymer which may encompass PEG-b-P(L-Arg) in general. However, the documents do not specifically disclose PEG-b-P(L-Arg) (or do not disclose PEG-b-P(L-Arg) specified with a specific chemical structural formula). The documents do not disclose or suggest the way to efficiently produce such a polymer or a composition containing the polymer and a polyanionic polymer or a feature in which a polyion complex (PIC) of the polymer and a polyanionic polymer can form stable micelles or high molecular micelles in an aqueous medium. In addition, the documents do not suggest that L-Arg, which may be a substrate of iNOS produced in the presence of macrophages, can be provided. Meanwhile, it is known that a PIC of a polyanionic amino acid (PEG-b-PAsp) and a polycationic amino acid (PEG-b-PLys), which is a different system from that of the present invention, forms micelles (for example, see Harada et al., Macromolecules, 28, 5294-99 (1995)).

With regard to polyarginine, conventional block copolymers containing poly(arginine) segments contain by-products such as diguanidine and do not undergo quantitative guanidino group substitution (see Michael S. Bernatowicz, et al., Journal of Organic Chemistry, 57, 2497-2502, (1992)). Although a block copolymer in which a poly(arginine) side chain has a Z protecting group has been reported, a harsh condition is required to eliminate the Z protecting group. As a result, although deprotection could be actually carried out in a milligram scale, deprotection in a gram scale results in cleavage of the peptide main chain (ERIC P. HOLOWKA, et al., Nature materials, 6, 52-57, 2007). Further, due to the production method which produces copolymers having other than guanidino groups in side chains and which does not widely control the molecular weight distribution, there have been concerns such that the L-arginine monomers after cleavage of peptide bonds do not work as a substrate of iNOS or stable PIC micelles cannot be formed. In addition, conventional PIC micelles have low stability under physiological conditions and particles are destroyed due to a blood salt concentration, polyanions and fatal bovine serum (FBS). Further, conventional PIC micelles have been designed with the aim of delivery of proteins and nucleic acids to tumor tissue, and thus nanoparticles per se have not been examined for anticancer activity or the like.

With regard to the problems accompanying to the conventional art, the inventors of the present invention have found that, according to the present invention, PEG-b-P(L-Arg) or P(L-Arg)-b-PEG-b-P(L-Arg) produced by a specific production method has narrow molecular weight distribution and that PIC micelles formed with the block copolymer and a polyanionic polymer in an aqueous medium has a nanometer (nm)-scale average diameter which is stable and is suitable for incorporation in tumor tissue.

Thus, various embodiments indicated below of the present invention are provided as means for solving the above problems, although the present invention is not limited to the following embodiments.

(1) A polyion complex (PIC) containing a polycationic polymer and a polyanionic polymer, wherein the polycationic polymer is a copolymer represented by formula (I):

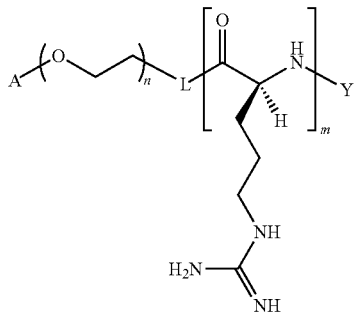

wherein:

A represents (i) hydrogen or an unsubstituted or substituted $C_1$-$C_{12}$ alkyl group, wherein a substituent when the group is substituted represents a formyl group, a group of the formula $R^1R^2CH$— (where $R^1$ and $R^2$ independently represent $C_1$-$C_4$ alkoxy or $R^1$ and $R^2$ together represent —$OCH_2CH_2O$—, —$O(CH_2)_3O$— or —$O(CH_2)_4O$—) or (ii) the formula

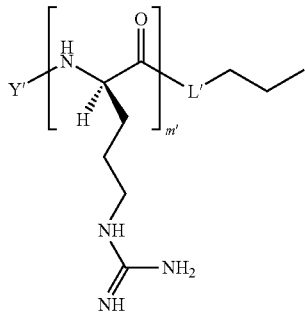

wherein L and L' independently represent a linkage group; Y and Y' independently represent H, $C_{1-21}$ alkylcarbonyl, substituted $C_{1-4}$ alkylcarbonyl, unsubstituted or substituted $C_{3-7}$ cycloalkylcarbonyl, unsubstituted or substituted arylcarbonyl, or unsubstituted or substituted 5- or 6-membered heteroarylcarbonyl, wherein a substituent of the substituted $C_{1-4}$ alkylcarbonyl is selected from the group consisting of a halogen atom, hydroxyl, carboxyl, unsubstituted or substituted $C_{3-7}$ cycloalkyl, unsubstituted or substituted aryl, unsubstituted or substituted 5- or 6-membered heteroaryl, unsubstituted or substituted adamantyl and an unsubstituted or substituted cholesterol residue, wherein a substituent when the foregoing substituents are substituted may be $C_{1-4}$ alkyl, $C_{1-4}$ alkyloxy, hydroxyl, carboxyl, cyano, nitro, a halogen atom or mono- or di-$C_{1-4}$ alkylamino;

m and m' are independently an integer of 5 to 300;

n is an integer of 5 to 1,000; and up to 80% of m or m' amidino groups (C(=NH)NH$_2$) may be H, the polyanionic polymer is selected from the group consisting of a polyanionic polysaccharide, a polyanionic polypeptide, a poly(acrylic acid) and a poly(methacrylic acid), and the PIC when dissolved or dispersed in water is in the form of PIC micelles having a nanometer (nm)-scale average particle diameter.

(2) The polyion complex according to the embodiment (1), wherein A is defined by (i).

(3) The polyion complex according to the embodiment (1), wherein A is defined by (ii).

(4) A composition for providing a substrate L-Arg of inducible NO synthase derived from activated cells in mammalian tissue, the composition containing the polyion complex according to any one of the embodiments (1) to (3) as an active ingredient.

(5) The composition according to the embodiment (4), wherein the activated cells in mammalian tissue are macrophages in or in the vicinity of tumor tissue.

(6) The composition according to the embodiment (4), wherein the activated cells in mammalian tissue are macrophages activated due to intramyocardial inflammation.

(7) A composition for prophylaxis or therapy of tumors in mammalian tissue, the composition containing the polyion complex according to any one of the embodiments (1) to (3) as an active ingredient.

(7') A method for prophylaxis or therapy of tumors in a mammal, the method including administering an antitumor effective amount of the polyion complex according to any one of the embodiments (1) to (3), preferably according to the embodiment (2), to a mammal in need thereof.

(8) A method for producing a block copolymer represented by formula (I):

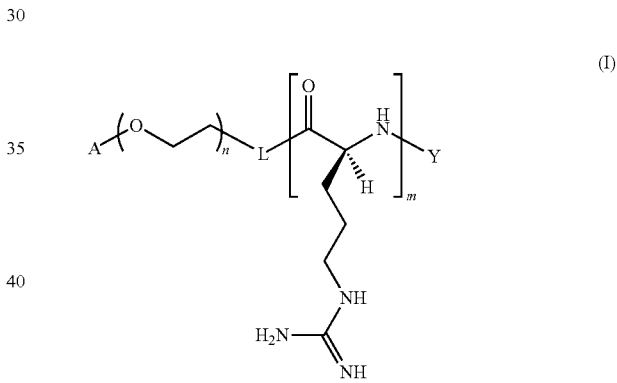

wherein:

A represents (i) hydrogen or an unsubstituted or substituted $C_1$-$C_{12}$ alkyl group, wherein a substituent when the group is substituted represents a formyl group, a group of the formula $R^1R^2CH$— (where $R^1$ and $R^2$ independently represent $C_1$-$C_4$ alkoxy or $R^1$ and $R^2$ together represent —$OCH_2CH_2O$—, —$O(CH_2)_3O$— or —$O(CH_2)_4O$—) or (ii) the formula

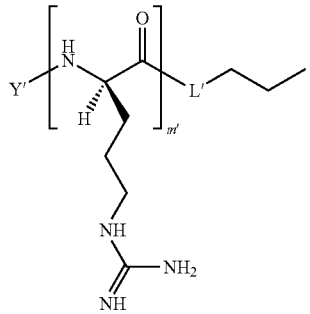

wherein L and L' independently represent a linkage group;

Y and Y' independently represent H, $C_{1-21}$ alkylcarbonyl, substituted $C_{1-4}$ alkylcarbonyl, unsubstituted or substituted $C_{3-7}$ cycloalkylcarbonyl, unsubstituted or substituted arylcarbonyl, or unsubstituted or substituted 5- or 6-membered heteroarylcarbonyl, wherein a substituent of the substituted $C_{1-4}$ alkylcarbonyl is selected from the group consisting of a halogen atom, hydroxyl, carboxyl, unsubstituted or substituted $C_{3-7}$ cycloalkyl, unsubstituted or substituted aryl, unsubstituted or substituted 5- or 6-membered heteroaryl, unsubstituted or substituted adamantyl and an unsubstituted or substituted cholesterol residue, wherein a substituent when the foregoing substituents are substituted may be $C_{1-4}$ alkyl, $C_{1-4}$ alkyloxy, hydroxyl, carboxyl, cyano, nitro, a halogen atom or mono- or di-$C_{1-4}$ alkylamino;

m and m' are independently an integer of 5 to 300;

n is an integer of 5 to 1,000; and up to 80% of m or m' amidino groups ($C(=NH)NH_2$) may be H, the method including a step of reacting a block copolymer represented by formula (II);

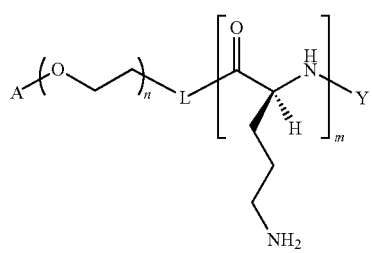

(II)

wherein:

A (i)' is as defined in (i) for formula (I) above or (ii)' represents the formula:

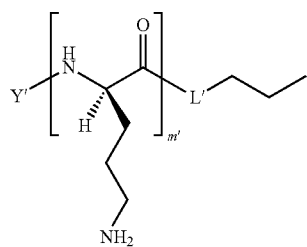

and L, L', Y, Y', n, m and m' are as defined for formula (I) above, with N,N'-bis(tert-butoxycarbonyl)-1H-pyrazole-1-carboxamidine optionally in an inert solvent in order to convert a δ-amino group in a segment derived from ornithine to a guanidino group.

(9) The method for producing a block copolymer according to the embodiment (8), wherein A in formula (II) is defined by (i)'.

(10) The method for producing a block copolymer according to the embodiment (8), wherein A in formula (II) is defined by (ii).

(11) A block copolymer represented by formula (III):

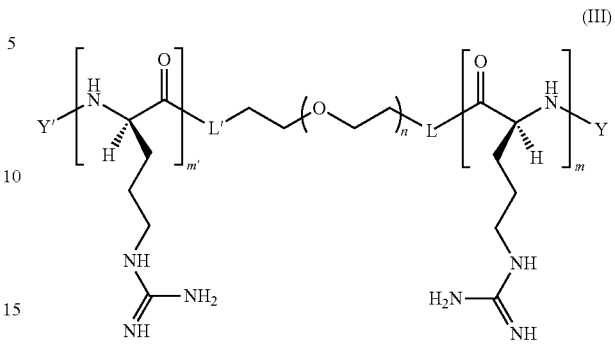

(III)

wherein:

L and L' independently represent a linkage group;

Y and Y' independently represent H, $C_{1-21}$ alkylcarbonyl, substituted $C_{1-4}$ alkylcarbonyl, unsubstituted or substituted $C_{3-7}$ cycloalkylcarbonyl, unsubstituted or substituted arylcarbonyl, or unsubstituted or substituted 5- or 6-membered heteroarylcarbonyl, wherein a substituent of the substituted $C_{1-4}$ alkylcarbonyl is selected from the group consisting of a halogen atom, hydroxyl, carboxyl, unsubstituted or substituted $C_{3-7}$ cycloalkyl, unsubstituted or substituted aryl, unsubstituted or substituted 5- or 6-membered heteroaryl, unsubstituted or substituted adamantyl and an unsubstituted or substituted cholesterol residue, wherein a substituent when the foregoing substituents are substituted may be $C_{1-4}$ alkyl, $C_{1-4}$ alkyloxy, hydroxyl, carboxyl, cyano, nitro, a halogen atom or mono- or di-$C_{1-4}$ alkylamino;

m and m' are independently an integer of 5 to 300;

n is an integer of 5 to 1,000; and up to 80% of m or m' amidino groups ($C(=NH)NH_2$) may be H.

Effects of Invention

According to the present invention, PIC micelles, particularly PIC micelles of a diblock copolymer represented by formula (I) wherein A is defined by (i) and preferably a polyanionic polysaccharide, more preferably chondroitin sulfate or hyaluronic acid, most preferably chondroitin sulfate can be present as monodispersed and stable PIC micelles in blood. Such PIC micelles are incorporated by macrophages in tumor, thereby significantly producing NO. Therefore, nanoparticles per se exhibit anticancer or antitumor activity without carrying anticancer agents or proteins, nucleic acids and the like having anticancer activity, and thus are a promising candidate substance which can be used alone or in combination with another anticancer agent in cancer therapy.

BRIEF DESCRIPTION OF DRAWINGS

FIG. 1 is L a $^1$H-NMR spectrogram of L-Orn(Z)-NCA.

FIG. 2 is a size fractionation chromatogram (SEC) of PEG-b-P(L-Orn(Z)).

FIG. 3 is a $^1$H-NMR spectrogram of PEG-b-P(L-Orn(Z))

FIG. 4 is a $^1$H-NMR spectrogram of PEG-b-P(L-Orn).

FIG. 5 is a $^{13}$C-NMR spectrogram of PEG-b-P(L-Orn).

FIG. 6 is a $^1$H-NMR spectrogram of PEG-b-P(L-Arg(Boc$_2$)).

FIG. 7 is a size fractionation chromatogram (SEC) of PEG-b-P(L-Arg).

FIG. 8 is a $^1$H-NMR spectrum of PEG-b-P(L-Arg) (degree of polymerization: m=30).

FIG. 9 is a $^{13}$C-NMR spectrogram of PEG-b-P(L-Arg).

FIG. 10 is a graph showing the change in the substitution rate to guanidino groups with reaction time.

FIG. 11 is a $^1$H-NMR spectrogram of PEG-b-P(L-Arg) (degree of polymerization m=62).

FIG. 12 is a $^1$H-NMR spectrogram of PEG-b-P(D-Arg).

FIG. 13 is a $^1$H-NMR spectrogram of PEG-b-P(L-Lys-Gua).

FIG. 14 is a graph showing the DLS evaluation result of PIC micelles formed from PEG-b-P(L-Arg) and chondroitin sulfate C.

FIG. 15 is a graph showing the result of NO production evaluation by reaction of polyarginine and iNOS enzyme in a buffer.

FIG. 16 is a graph showing the result of NO production evaluation from RAW264.7 macrophages (*p<0.05, n=3).

FIG. 17 is a graph showing the change in the relative body weight of tumor-bearing mice responding to intravenous administration of L-PArg-CS/m (n=4).

FIG. 18 is a graph showing the change in the tumor volume of tumor-bearing mice responding to intravenous administration of L-PArg-CS/m (*p<0.05, **p<0.01, n=4).

FIG. 19 is $^1$H-NMR spectrograms of POrn(Z)-b-PEG-b-POrn(Z) and POrn-b-PEG-b-POrn.

FIG. 20 is $^1$H-NMR spectrograms of PArg(Boc2)-b-PEG-b-PArg(Boc2) and PArg-b-PEG-b-PArg.

FIG. 21 is photos substituting a figure representing gelation behavior of PIC(PMNT-b-PEG-b-PMNT+PAAc or PMNT-b-PEG-b-PMNT/PArg-b-PEG-b-PArg+PAAc).

FIG. 22 is photos substituting a figure representing tube formation behavior of PEG-b-PArg/CS and PArg-b-PEG-b-PArg/CS in HUVECs.

FIG. 23 is a graph showing the results of echocardiogram and left ventricular ejection fraction (LVEF) analysis at 4 weeks after myocardial infarction (MI).

FIG. 24 is photos substituting a figure representing histological evaluation results of heart tissue at 4 weeks after MI by Masson trichrome staining.

DESCRIPTION OF EMBODIMENTS

Technical terms used herein are used to represent the meanings which are usually used in the art unless stated otherwise.

<PIC>

The PIC of the present invention contains a polycationic polymer, which is a block copolymer of formula (I) (PEG-b-P(L-Arg) or P(L-Arg)-b-PEG-b-P(L-Arg)), and a polyanionic polymer, and preferably consists essentially of or consists of the copolymer and the polyanionic polymer.

<PIC Micelles>

Further, it is understood that the PIC containing the block copolymer of formula (I) (PEG-b-P(L-Arg) or P(L-Arg)-b-PEG-b-P(L-Arg)) and the polyanionic polymer is formed in an aqueous medium and forms a PIC moiety by electrostatic interaction between a poly(L-arginine) (which may be referred to as P(L-Arg)) segment in the copolymer and the polyanionic polymer, thereby forming nano-scale polymer micelles including the PIC moiety as a core and a poly (ethylene glycol) moiety of the copolymer as a shell (for example, see the result in Example 9, "Preparation of polyion complex micelles", of DLS analysis of the PIC micelle aqueous solution). The aqueous medium may be pure water or ion-exchange water or a buffered solution thereof, an aqueous solution containing a water-soluble organic solvent (such as N,N-dimethylformamide or dimethylsulfoxide) or the like.

The linkage groups L and/or L' in formulae (I), (II) and (III) may be any organic divalent group as far as the group does not have adverse effect on formation of the polyion complex micelles. The linkage groups generally represent —O—$(CH_2)_a$—NH—, —O—$(CH_2)_a$—O—, —$(CH_2)_a$—NH— or —$(CH_2)_a$—O—, preferably —O—$(CH_2)_a$NH— or —$(CH_2)_a$—NH— (wherein a is an integer of 1 to 6, preferably 1 to 3). The orientation of the linkage group L is the forward direction of each moiety in each structural formula. For example, in case of —O—$(CH_2)_a$NH—, the bond on the side of —O—$(CH_2)$ covalently binds to methylene in formula (I) and the moiety NH— covalently binds to the carbonyl group. Meanwhile, the orientation of L' is opposite to that of L.

Y represents H, $C_{1-21}$ alkylcarbonyl, substituted $C_{1-4}$ alkylcarbonyl, unsubstituted or substituted $C_{3-7}$ cycloalkylcarbonyl, unsubstituted or substituted arylcarbonyl or unsubstituted or substituted 5- or 6-membered heteroarylcarbonyl.

The alkyl which is in the above respective groups or forms a part of the above respective groups may be linear or branched and examples thereof include, but are not limited to, those corresponding among methyl, ethyl, propyl, isopropyl, butyl, sec-butyl, tert-butyl, pentyl, hexyl, heptyl, nonyl, undecyl, tridecyl, heptadecyl, nonadecyl and the like. Preferably, the alkyl is selected from $C_{1-6}$ alkyls. The $C_{3-7}$ cycloalkyl may be cyclopropyl, cyclobutyl, cyclopentyl, cyclohexyl or cycloheptyl. The aryl may be phenyl or naphthyl. The 5- or 6-membered heteroaryl is an unsaturated heterocyclic group containing 1 or 2 heteroatoms, which may be the same or different, selected from oxygen, nitrogen and sulfur atoms, and may be thienyl, furyl, pyranyl, pyrrolyl, isoxazole, pyrazolyl, imidazolyl, pyridyl, pyrazinyl or pyrimidinyl, wherein the heterocyclic ring may be benzocondensed. Examples of such a condensed ring include isoindolyl, indolyl, quinolyl, isoquinolyl, quinoxalinyl, quinazolinyl and phenanthridinyl.

A substituent of the substituted $C_{1-4}$ alkylcarbonyl is selected from the group consisting of a halogen atom (Cl, F, Br, I), hydroxyl, carboxyl, unsubstituted or substituted $C_{3-7}$ cycloalkyl, unsubstituted or substituted aryl, unsubstituted or substituted 5- or 6-membered heteroaryl, unsubstituted or substituted adamantyl and an unsubstituted or substituted cholesterol residue, and a substituent when the foregoing substituents are substituted may be $C_{1-4}$ alkyl, $C_{1-4}$ alkyloxy, hydroxyl, carboxyl, cyano, nitro, a halogen atom or mono- or di-$C_{1-4}$ alkylamino. The latter substituents may be also applied to the substituted $C_{3-7}$ cycloalkylcarbonyl, the substituted arylcarbonyl and the substituted 5- or 6-membered heteroarylcarbonyl.

Among the above definitions, the cholesterol residue may be a residue of a cholesterol molecule from which H is eliminated on any of carbons at positions 22 to 27 or from which a hydrocarbon chain including any of carbons at positions 22 to 27 is eliminated. Examples of the alkylcarbonyl substituted with such a residue includes cholic acid and chenodeoxycholic acid. Y is preferably $C_{1-6}$ alkylcarbonyl.

m and m' may independently be, in view of the stability of PIC micelles formed from the copolymer and the anionic polymer in an aqueous medium, an integer of preferably 10 to 200, more preferably 15 to 150 and most preferably 15 to 100.

Similarly, n may be an integer of preferably 20 to 800, more preferably 30 to 500 and most preferably 40 to 400.

Generally, up to 80%, preferably up to 60%, more preferably up to 30% and most preferably up to 10% of the m and m' amidino groups (C(=NH)NH$_2$) in formula (I) may be independently H, and particularly preferably all of m and m' groups are amidino groups.

The polyanionic polymer can form a stable PIC with the copolymer represented by formula (I) in an aqueous medium, wherein the PIC can form stable polymer micelles. Specific polyanionic polymer is, but is not limited to, one or more selected from the group consisting of polyacrylic acids, polymethacrylic acids, polysulfonic acids, polyanionic polysaccharides, anionic proteins and the like. Preferably, the polyanionic polymer is chondroitin sulfate, carrageenan, heparin, carboxymethyl dextran, xanthan gum, hyaluronic acid, polyaspartic acid, polyglutamic acid and in view of the stability, chondroitin sulfate may be mentioned as a particularly preferable polyanionic polymer. The molecular weight of the polyanionic polymer may have different optimal values depending on the type of the polymers and is not limited. However, the polyacrylic acid preferably has Mn of 200 to 1000000, preferably 500 to 100000, more preferably 1000 to 10000. The polyanionic polysaccharide, for example, chondroitin sulfate has Mn or Mw of 500 to 1000000, preferably 1000 to 100000, and the anionic polypeptide, for example, polyaspartic acid has Mn or Mw of 500 to 1000000, preferably 1000 to 100000. The polyanionic acid may be commercially available and may be optionally purified.

<Production of Block Copolymer>

The block copolymer represented by formula (I) for formation of the PIC may contain corresponding PEG segments and P(L-Arg) segments produced by any methods as far as the purpose of the present invention is fulfilled. However, it is preferable that the block copolymer has narrow molecular weight distribution and allows formation from the block copolymer and a polyanionic polymer in an aqueous medium of PIC micelles which are nanoparticles having an average diameter suitable for uptake by tumor tissue. Such a copolymer may be produced according to the above embodiment (8) of the present invention.

A precursor of formula (II);

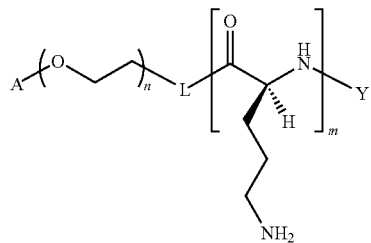

(II)

wherein A, L, Y, m and n are as defined in formula (II) above;

may be preliminarily prepared, and conversion of a δ-amino group in a segment derived from L-ornithine in the formula to a guanidino group may be carried out with an agent for the guanidino conversion, N,N'-bis(tert-butoxycarbonyl)-1H-pyrazole-1-carboxamidine, thereby providing the copolymer. The production is typically carried out according to the synthesis scheme shown below by forming a salt between the copolymer represented by formula (II) and trifluoroacetic acid (TFA) and carrying out guanidino conversion in the presence of an appropriate base in an inert solvent or in a solvent serving as a base and a solvent such as N-methylpyrrolidone or dimethylsulfoxide.

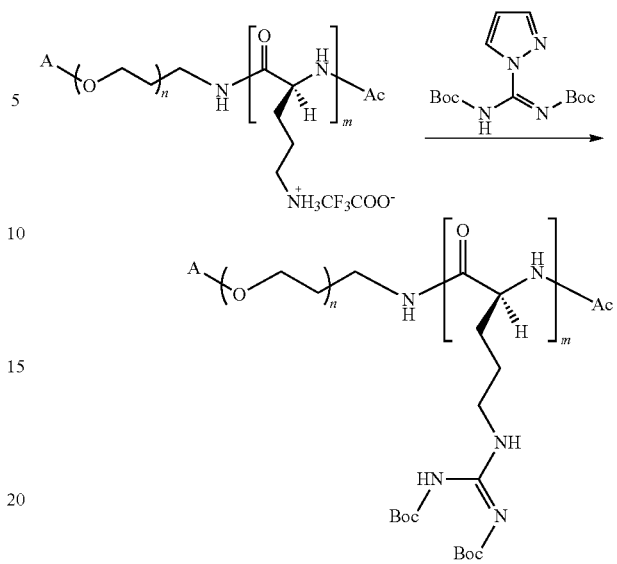

When A in the first formula in the above reaction scheme is defined by (ii)' as in formula (II) above, the δ-amino group in the segment derived from ornithine corresponding to the repeating unit of m' in the formula indicated therein is in the form of a salt of trifluoroacetic acid, similar to that in the repeating unit of m. After guanidino conversion, A in the last formula in the reaction scheme has the δ-amino group in the segment derived from ornithine corresponding to the repeating unit of m', which is a di-Boc-protected amidino group.

The protecting group tert-butoxycarbonyl (Boc) in the moiety derived from the agent for guanidino conversion is then eliminated to obtain the desired block copolymer of formula (I). While the elimination reaction may be carried out under any condition as far as the condition does not adversely affect the peptide bonds of the copolymer and the like, it is preferable that the elimination reaction is carried out under the condition where TFA is used.

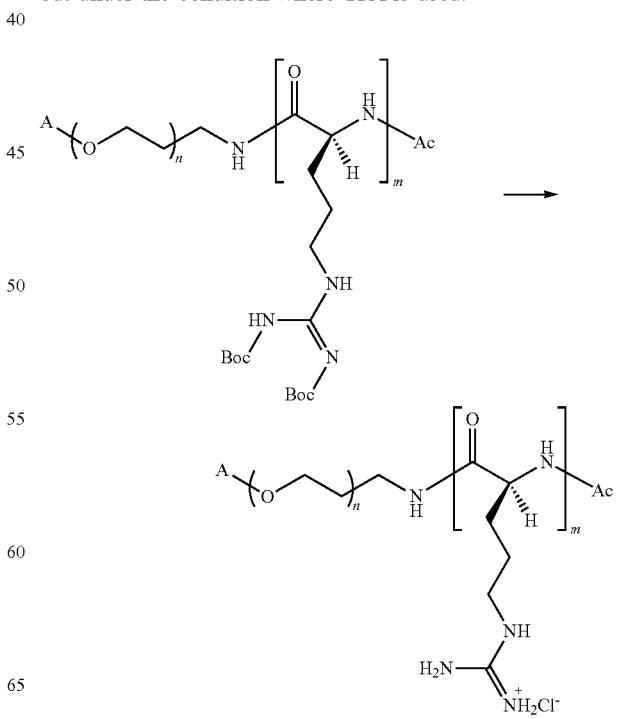

Further, in order to provide the copolymer of the present invention having narrow molecular weight distribution, the precursor copolymer represented by formula (II) (wherein, for example, A in formula (II) is represented by (i)') is preferably produced according to the following synthesis scheme.

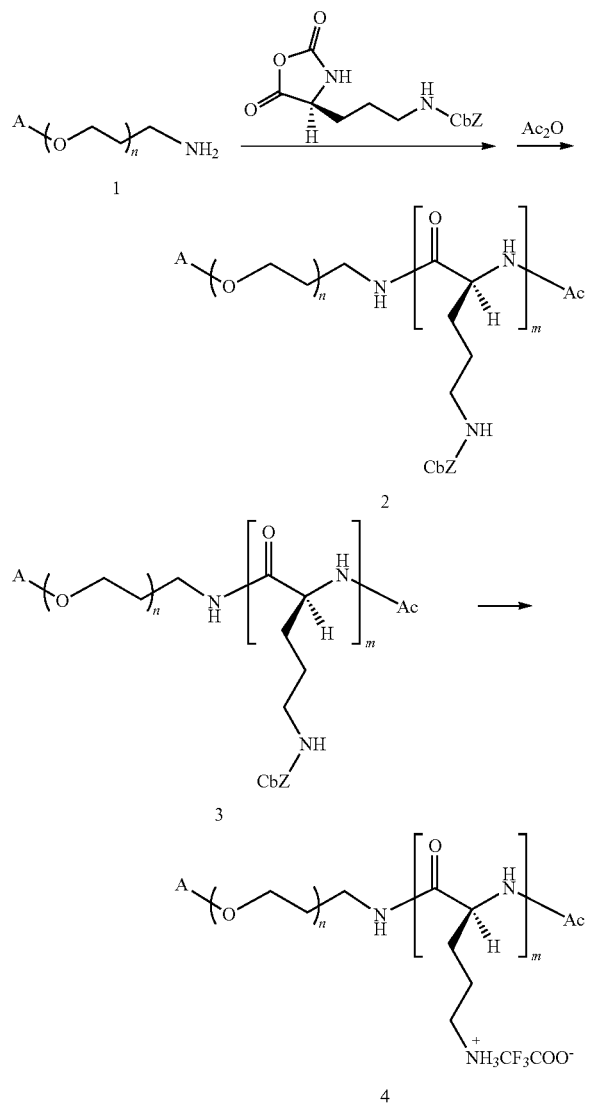

Compound 1 used is one that is commercially available or prepared according to the production method thereof and has molecular weight distribution as narrow as possible. Compound 1 is subjected to a known method per se in which the compound is subjected to living ring-opening polymerization with an amino acid anhydride of ornithine acid of which amino group is protected and then the reaction is terminated with a living terminal modifier such as acetic anhydride to produce compound 2. The amino protecting group in the poly(L-ornithine) segment is further eliminated.

According to the reaction/treatment using compound 1 as a starting material, a precursor copolymer having poly(L-ornithine) segments and having very narrow molecular weight distribution can be provided.

Thus, it is possible to provide the finally obtained block copolymer represented by formula (I) according to the present invention that has molecular weight distribution of 1.01 to 1.20, preferably 1.01 to 1.06.

Meanwhile, when A in formula (II) is defined by (II)', compound 1, which is a starting material in the above reaction scheme, used is $NH_2CH_2CH_2-(OCH_2CH_2)_nNH_2$, and the A moiety in compounds 2 to 4 may be repeating units corresponding to m repeating units.

The thus obtained triblock copolymer wherein A in formula (II) is defined by (ii)' is represented by the following formula (III):

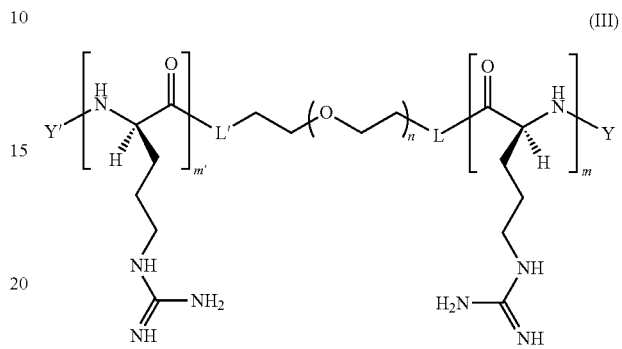

wherein L, L', Y, Y', m, m' and n are as defined in formula (III) above;
which has not disclosed in any prior art documents to the best of the inventor's knowledge.

<Preparation of PIC Micelles>

The PIC micelles according to the present invention may be prepared by adjusting the block copolymer represented by formula (I) and the polyanionic polymer so that the ratio of the number (referred to as C) of amino groups or guanidino groups of the former compound/the number (A) of carboxyl groups and/or sulfo groups of the latter compound is 0.5 to 2.50, dissolving and mixing the compounds in a buffered aqueous solution (pH=7.2 to 7.5) and leaving the mixture to stand for a certain period of time (usually for 30 minutes or more at room temperature). During the preparation, the micelle aqueous solution obtained with the block copolymer of formula (I) wherein A is defined by (i) may be subjected to dynamic light scattering (DLS) analysis, thereby generally obtaining micelle particles having an average particle diameter of about 20 nm to about 50 nm. Meanwhile, the PIC micelle aqueous solution obtained from the triblock copolymer of formula (I) wherein A is defined by (ii) or the triblock copolymer represented by formula (III) and the polyanionic polymer may be subjected to DLS analysis, thereby generally obtaining micelle particles having an average particle diameter of about 40 to 70.

The thus obtained PIC micelles can be separated with separation means such as centrifugation, can be stored as a dry composition by lyophilization and can be optionally reconstituted in an aqueous medium. The dry composition can optionally provide a PIC micelle aqueous solution containing a physiologically acceptable diluent or excipient. The diluent may be sterilized water, saline, a solution containing a physiologically acceptable buffer and the like. The excipient may be, for example, sorbitol, dextrin, dextrose, mannitol, amino acid (such as glycine, isoleucine, valine, methionine and glutamic acid) and the like.

The aqueous solution may be administered to a mammal in need thereof, particularly to a human, through vein or artery or the aqueous solution or the dry composition may be directly administered to the tumor site. The PIC micelles can be accumulated at tumor tissue and exhibit antitumor effect by producing NO in situ. The dose may be appropriately decided by a specialist by referring to the results of Test Examples described hereinbelow or similar tests.

Meanwhile, a PIC micelle aqueous solution of the triblock copolymer of formula (III) alone or a mixture thereof with the triblock copolymer disclosed in WO2015/118993A, typically PMNT-PEG-PMNT or those encompassing thereof represented by the following general formula (the ratio of the L-Arg units of the former copolymer to the TEMPO units of the latter copolymer may be 5 to 1:1 to 5) as described in Example 11 and a specific anionic polymer causes gelation under physiological pH and at or above 37° C. Therefore, the PIC micelle aqueous solution may be directly administered to the physiological site (such as cardiac muscle and joints) at which the PIC is sought to be retained, so that the disease or disorder in which inflammation is involved may be treated. With regard to the mode of administration, WO2013/111801A, WO2013/111801A and WO2014/199982A may be referred to which are patent applications in which the inventors of the present invention are involved. The patent documents are entirely incorporated herein by reference.

According to the main disclosures, PMNT-PEG-PMNT can be synthesized according to the following synthesis scheme.

The triblock copolymer encompassing such PMNT-PEG-PMNT can be represented by the following general formula according to the technical concept.

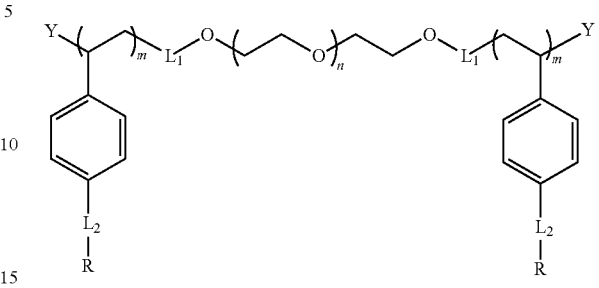

wherein:
$L_1$'s represent the same or different linkage groups:
$L_2$'s are independently —$C_{1-6}$ alkylene-NH—($C_{1-6}$ alkylene)$_q$-, wherein q is 0 or an integer of 1; and
R's are independently as follows: at least 20% of the total n R's represent a residue of a cyclic nitroxide radical compound selected from the group consisting of 2,2,6,6-tetramethylpiperidine-1-oxyl-4-yl, 2,2,5,5-tetramethylpyr-

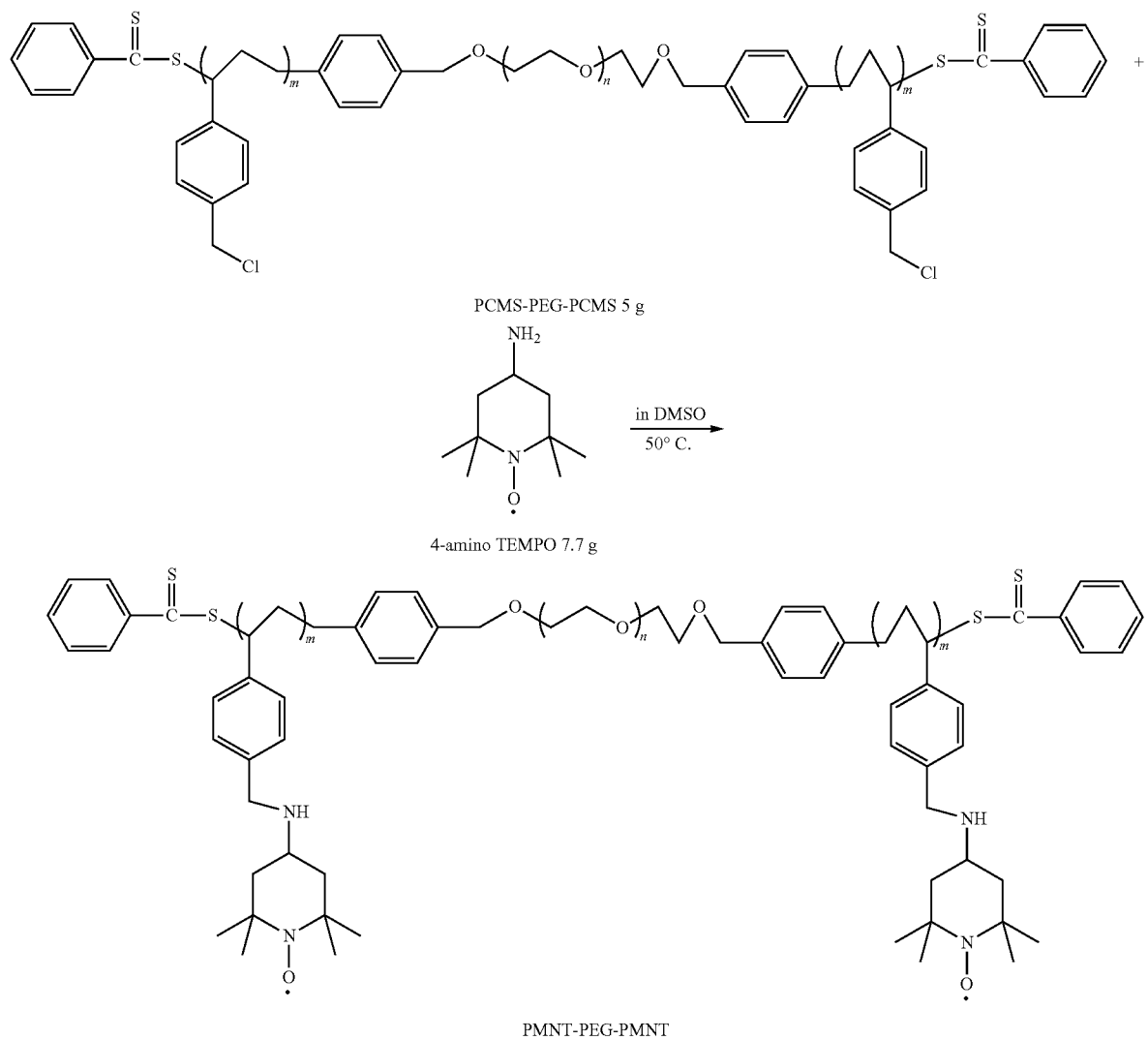

rolidine-1-oxyl-3-yl, 2,2,5,5-tetramethylpyrroline-1-oxyl-3-yl, 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl and the rest of R's, when present, are a hydrogen atom, a halogen atom or a hydroxy group;

Y's are independently selected from the group consisting of H, phenylthiocarbonylthio that may be substituted with $C_{1-6}$ alkyl, $C_{1-6}$ alkylthiocarbonylthio, $C_{1-6}$ alkyloxythiocarbonylthio and SH;

m's are independently an integer of 3 to 1,000; and n is an integer of 5 to 5,000.

In the preferable embodiments of the above general formula, $L_1$'s are independently selected from the group consisting of a single bond, —S—$(CH_2)_c$—, —S—$(CH_2)_c$CO—, —$(CH_2)_c$S—, —CO$(CH_2)_c$S—,

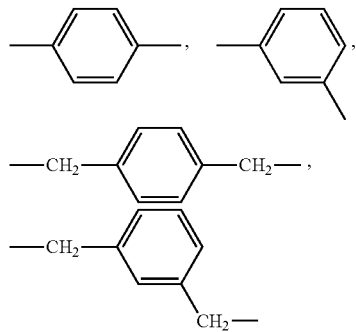

wherein c is an integer of 1 to 5, provided that when the linkage group has an orientation, for example, is —S—$(CH_2)_c$—, $L_1$ on the left hand side of the above formula is linked in the direction as indicated, namely the side of the S atom binds to $CH_2$ and the side of $CH_2$ binds to the O atom, while $L_1$ on the right hand side is linked in the reverse direction.

Y is preferably H or selected from the group consisting of —SH,

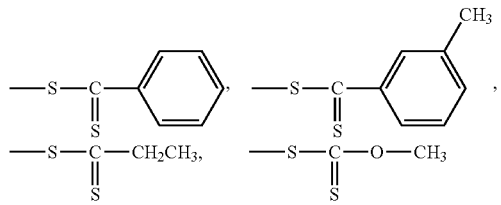

R's are independently as follows: preferably 80%, more preferably at least 90% and most preferably about 100% of the total n R's represents a residue of a cyclic nitroxide radical compound selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl and the rest of R's, when present, are a hydrogen atom, a halogen atom or a hydroxy group;

m's are independently and preferably an integer of 3 to 100, more preferably 3 to 50; and n is an integer of preferably 5 to 1000, more preferably 10 to 200.

The PEG-b-P(L-Arg) or P(L-Arg)-PEG-P(L-Arg) block copolymer per se can be used as, in addition to the above purposes, 1) a polycation for gene delivery; 2) a surface coating agent of inorganic nanoparticles such as silica nanoparticles, metal nanoparticles such as gold nanoparticles and magnetic nanoparticles; 3) a surface coating agent of bio-devices; and 4) an agent for incorporating a drug or the like to cells. The PIC micelles can be used as, in addition to the above purposes, 1) a DDS carrier for drug delivery; and 2) a DDS carrier for gene delivery.

EXAMPLES

The present invention is hereinafter specifically described by way of specific examples which do not mean to limit the present invention.

Example 1

Synthesis of L-Orn(Z)-NCA which is an amino acid anhydride (N-carboxy anhydride, NCA) of Nδ-benzyloxycarbonyl-L-ornithine (L-Orn(Z))

L-Orn(Z)-NCA was synthesized according to the following synthesis scheme 1;

Scheme 1:

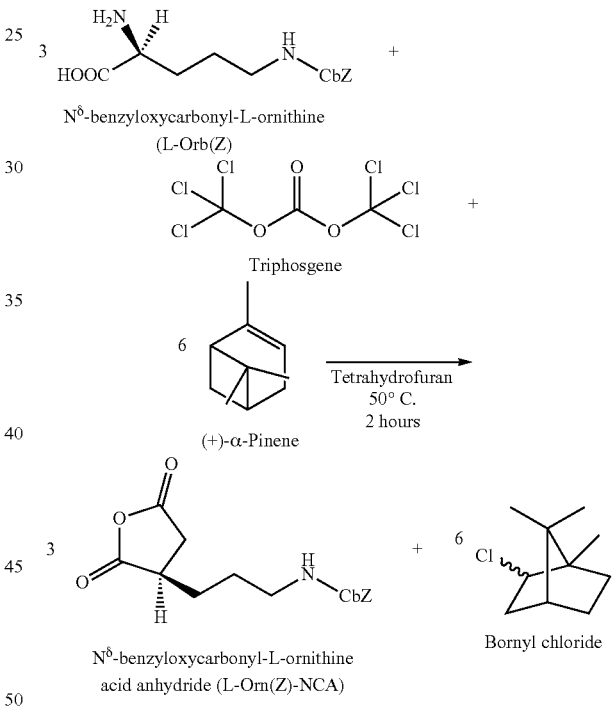

L-Orn(Z) (15.0 g, 56.3 mmol) was added to a 500-mL pear-shaped reactor. After the reactor was vacuumed, the reactor was replaced with nitrogen gas three times to obtain a nitrogen atmosphere in the reactor. To the reactor, 150 mL tetrahydrofuran (THF) was added to disperse L-Orn(Z) therein and stirring was initiated. To the reactor, triphosgene (6.13 g, 20.7 mmol) dissolved in 25 mL THF was added. To the reactor, (+)-α-pinene (17.5 mL, 112.7 mmol) was added, heated to 50° C. and stirred for 1 hour. The reaction solution was evaporated in an evaporator, 200 mL of THF was further added which was again evaporated in an evaporator to remove protons in the reaction solution. The obtained off-white solid was recrystallized in a mixed solvent THF:hexane=1:3 to obtain needle-shaped crystals. The weight of the product was 10.5 g and the yield was 64%. The $^1$H-NMR spectrum of the obtained L-Orn(Z)-NCA is shown in FIG. 1.

Example 2

Synthesis of PEG-b-P(L-Orn(Z)) Block Copolymer

PEG-b-P(L-Orn(Z)) was synthesized according to the following synthesis scheme 2:

Scheme 2:

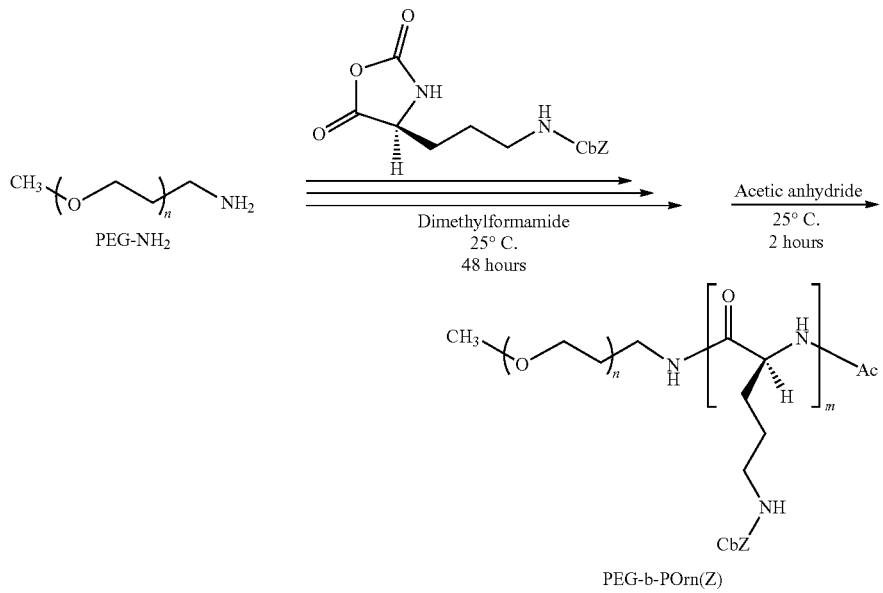

PEG-b-POrn(Z)

To a 500-mL flask reactor, polyethylene glycol (PEG-NH$_2$, molecular weight: 12,000, NOF Corporation) having a methoxy group at α-terminal and an amino group at ω-terminal (5.0 g, 0.42 mmol) and 30 mL benzene were added which were lyophilized overnight to remove the moisture in the reactor. The reactor was replaced with nitrogen to obtain a nitrogen atmosphere and a reaction solvent, 70 mL dimethylformamide (DMF) was added and stirring was initiated. L-Orn(Z)-NCA (3.9 g, 13 mmol) obtained according to Example 1 was dissolved in 30 mL DMF, added to the reactor and stirred at 25° C. for 48 hours. Thereafter, 4 mL acetic anhydride was added and stirred for 2 hours to acetylate the living terminal. The reaction solution was precipitated in 1.5 L diethyl ether on ice. After purification by reprecipitation operation with chloroform and diethyl ether repeated twice, white powder was obtained by lyophilization in benzene. The weight of the product was 8.1 g and the yield was 98%. The size fractionation chromatogram and the $^1$H-NMR spectrum of the obtained PEG-b-P(L-Orn(Z) block copolymer are shown in FIGS. 2 and 3, respectively. The molecular weight distribution with PEG being used as a standard was 1.07 and the P(L-Orn(Z)) segments had a degree of polymerization (m) of 30.

Example 3

Synthesis of PEG-b-P(L-Orn) Block Copolymer

PEG-b-P(L-Orn) was synthesized according to the following synthesis scheme 3:

Scheme 3:

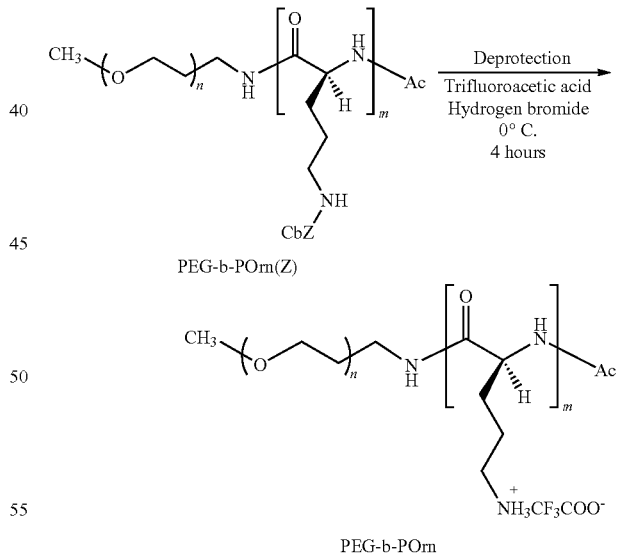

PEG-b-POrn

PEG-b-P(L-Orn(Z)) (3.0 g, 0.154 mmol) obtained according to Example 2 was placed in a 100-mL pear-shaped reactor followed by addition of 30 mL trifluoroacetic acid (TFA) and stirring. At 15 minutes after addition of TFA, 9 mL of a hydrogen bromide/acetic acid solution was added and stirred for 4 hours on ice. To the solution after the reaction, 40 mL distilled water was added and extraction was carried out with 1 L diethyl ether. Only the water phase was recovered and extracted again with 1 L diethyl ether. The ether extraction was carried out until the ether phase was neutral. The water phase after ether extraction was poured into a dialysis membrane with molecular weight cut off of 12 to 14,000, dialyzed against a 0.05% TFA aqueous solution for 24 hours and then against distilled water for 48 hours. The aqueous solution in the membrane after dialysis was lyophilized to obtain white powder. The weight of the product was 2.75 g and the yield was 95%. The PEG-b-P(L-Orn) block copolymer was recovered as a TFA salt. The TFA salt can be converted to a HCl salt by dialysis of PEG-b-P(L-Orn) against 0.01N HCl. The TFA salt block copolymer was used for guanidino conversion reaction and the HCl salt block copolymer was used for physical property evaluation. The $^1$H-NMR and $^{13}$C-NMR spectra of the obtained PEG-b-P(L-Orn) block copolymer are shown in FIGS. 4 and 5, respectively. The P(L-Orn) segments had a degree of polymerization (m) of 30.

Example 4

Synthesis of PEG-b-P(L-Arg(Boc$_2$)) Block Copolymer
PEG-b-P(L-ArgBoc$_2$)) was synthesized according to the following synthesis scheme 4:

Scheme 4:

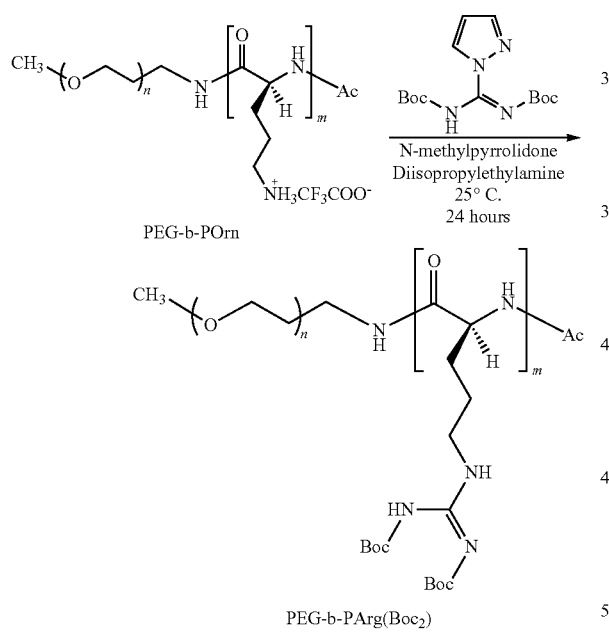

PEG-b-PArg(Boc$_2$)

To a 100-mL pear-shaped reactor, the TFA salt (2.5 g, 0.13 mmol) of the PEG-b-P(L-Orn) block copolymer obtained according to Example 3 and 50 mL of N-methylpyrrolidone were added. Then, N,N'-bis(tert-butoxycarbonyl)-1H-pyrazole-1-carboxamidine (PCX(boc$_2$)) (2.46 g, 7.9 mmol) serving as an agent for guanidino conversion and diisopropylethylamine (1.3 mL, 7.9 mmol) were added and stirred at 25° C. for 24 hours. The reaction solution was placed in a dialysis membrane with molecular weight cut off of 6 to 8,000 and dialyzed against DMF for 24 hours and then against methanol for 24 hours. The solution after dialysis was evaporated in an evaporator and the crude was lyophilized in benzene to obtain white powder. The weight of the product was 2.65 g and the yield was 88%. The $^1$H-NMR of the obtained PEG-b-P(L-Arg(Boc$_2$)) block copolymer is shown in FIG. 6. The P(L-Arg(Boc$_2$)) segments had a degree of polymerization (m) of 30 and a degree of substitution of 99%.

Example 5

Synthesis of PEG-b-P(L-Arg) Block Copolymer
PEG-b-P(L-Arg) was synthesized according to the following synthesis scheme 5:

Scheme 5:

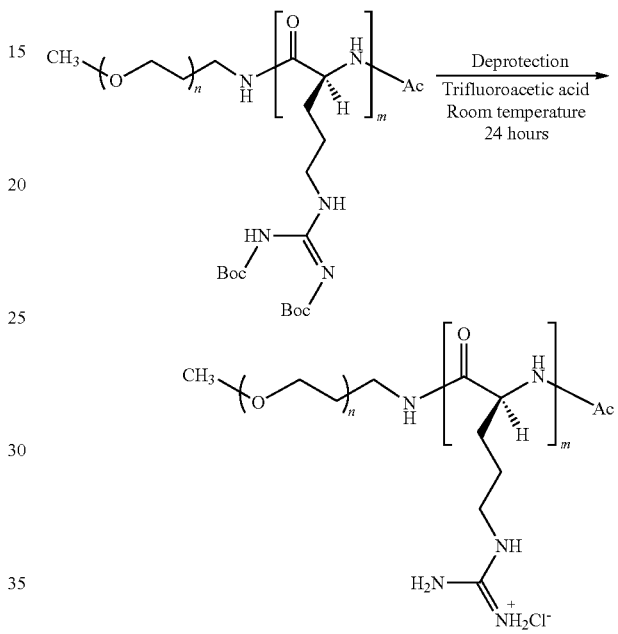

PEG-b-P(L-Arg(Boc$_2$)) (2.5 g, 0.109 mmol) obtained according to Example 4 was placed in a 100-mL pear-shaped reactor followed by addition of 50 mL trifluoroacetic acid (TFA) and stirring at room temperature for 24 hours. To the solution after the reaction, 50 mL distilled water was added and extraction was carried out with 1 L diethyl ether. Only the water phase was recovered and extracted again with 1 L diethyl ether. The ether extraction was carried out until the ether phase was neutral. The water phase after ether extraction was poured into a dialysis membrane with molecular weight cut off of 12 to 14,000, dialyzed against a 0.01 N HCl aqueous solution for 24 hours and then against distilled water for 48 hours. The aqueous solution in the membrane after dialysis was lyophilized to obtain white powder. The weight of the product was 1.88 g and the yield was 96%. The PEG-b-P(L-Arg) block copolymer was recovered as a HCl salt. The size fractionation chromatogram, and $^1$H-NMR and $^{13}$C-NMR spectra of the obtained PEG-b-P(L-Arg) block copolymer are shown in FIGS. 7, 8 and 9, respectively. The molecular weight distribution was 1.03 and the P(L-Arg) segments had a degree of polymerization (m) of 30 and a degree of substitution of 99%.

The substitution rate of guanidino groups was tracked over the reaction time and is shown in FIG. 10. When the agent for guanidino conversion used was PCX(Boc$_2$), about 80% of amino groups were converted to guanidino groups only after 1 hour of the reaction time and 99% of guanidino groups were introduced after 24 hours. Meanwhile, when a conventional agent for guanidino conversion, PCX.HCl, was used under the same conditions, only about 40% was substituted after 24 hours. When the agent for guanidino conversion used was N-(tert-butoxycarbonyl)-1H-pyrazole-1-carboxamidine (PCX(boc)), only about 5% was substituted to guanidino groups under the same conditions even after the reaction over 24 hours.

Example 6

Synthesis of PEG-b-P(L-Arg) Block Copolymer

In the same manner as in schemes in Examples 2 to 5 except that the amount of L-Orn(Z)-NCA obtained according to Example 2 was changed from 3.9 g to 7.8 g, PEG-b-P(L-Arg) was synthesized. The thus obtained block copolymer had P(L-Arg) segments having a degree of polymerization (m) of 62 and a degree of substitution to guanidino group of 99%. The $^1$H-NMR is shown in FIG. 11.

Example 7

Synthesis of PEG-b-P(D-Arg) Block Copolymer

In the same manner as in schemes in Examples 1 to 6 except that D-Orn(Z) was used instead of L-Orn(Z), PEG-b-P(D-Arg) was synthesized. The thus obtained block copolymer had P(D-Arg) segments having a degree of polymerization (m) of 58 and a degree of substitution to guanidino groups of 99%. The $^1$H-NMR is shown in FIG. 12.

Example 8

Synthesis of PEG-b-P(L-Lys-Gua) or PEG-b-P(L-homoArg) Block Copolymer

In the same manner as in schemes in Examples 1 to 6 except that Nδ-benzyloxycarbonyl-L-lysine (L-Lys(Z)) was used instead of L-Orn(Z), PEG-b-P(L-Lys-Gua) was synthesized. The block copolymer is a guanidyl substituted polylysine or poly(L-homoarginine) which is a PEG-b-poly(L-Lysine) block copolymer having polylysine segments of which ε-amino groups are substituted with guanidino groups. The thus obtained block copolymer had P(L-Lys-Gua) segments having a degree of polymerization (m) of 56 and a degree of substitution to guanidino groups of 99%. The $^1$H-NMR is shown in FIG. 13.

Example 9

Preparation of Polyion Complex Micelles

The PEG-b-P(L-Arg) block copolymer and chondroitin sulfate C sodium salt (CS: molecular weight: 50,000) were respectively dissolved in a Tris-HCl buffer (10 mM, pH 7.4) to prepare a PEG-b-P(L-Arg) polycation aqueous solution and a CS polyanion aqueous solution respectively having the concentration of 2 mg/mL. The PEG-b-P(L-Arg) polycation aqueous solution and the CS polyanion aqueous solution were mixed at arbitrary cation/anion ratios (C/A ratios), voltexed and left to stand for 30 minutes to prepare a PIC micelle aqueous solution. The C/A means [the number of amino groups or guanidino groups in the polycation]/[the number of carboxyl groups or sulfo groups in the polyanion]. The obtained PIC micelle aqueous solutions were subjected to dynamic light scattering (DLS) analysis, and nanoparticles having the highest scattering intensity and a low polydispersity index (PdI) were obtained when C/A was 1. The average particle diameter thereof is about 35 nm (FIG. 14).

<Test 1>

Reactivity of iNOS Enzyme with Polyarginine

Powders of block copolymers synthesized in Examples 6 to 9 were respectively dissolved in a HEPES-NaOH buffer (10 mM, pH 7.4) to prepare polymer aqueous solutions of 2 mg/mL. Each of the prepared polymer aqueous solution was mixed with a trypsin enzyme aqueous solution of 1 mg/mL and incubated at 37° C. for 24 hours. As a control, a buffer without trypsin enzyme and each of the polymer aqueous solutions were similarly mixed and incubated at 37° C. for 24 hours. The mixed solution after the incubation was incubated at 98° C. for 5 minutes to inactivate trypsin enzyme. The mixed solution and a buffer containing iNOS enzyme (Sigma-Aldrich) were mixed and incubated at 37° C. for 24 hours followed by assay of nitrite ions ($NO_2^-$) by Griess method (Dojindo Laboratories, product code: NK05). As a result, significant NO production after trypsin treatment was observed only for the PEG-b-P(L-Arg) block copolymer synthesized in Example 6 (FIG. 15). It was found that the level of NO production was similar to that of the system containing a PEG homopolymer (molecular weight: 12,000) and L-arginine at the same concentrations.

<Test 2>

Evaluation of NO Production from Macrophage Cells

RAW264.7 macrophage cells (American Type Culture Collection, ATCC (U.S.A.)) were used. The medium used was Dulbecco's modified Eagle's medium (DMEM) supplemented with 10% fatal bovine serum (FBS) and antibiotics (ampicillin, streptomycin and neomycin). To a 24-well plate, RAW264.7 macrophages were seeded at a cell density of 5,000 cells/well and incubated overnight at 37° C. and 5% $CO_2$ concentration. Thereafter, the PIC micelle aqueous solution prepared according to the method in Example 9 was added to the wells so that the arginine concentration in micelles was 1 mM and incubated for 72 hours. Thereafter, lipopolysaccharide (LPS) at a concentration of 10 ng/mL was added and incubated for 6 hours to activate the macrophages. After the incubation, the supernatant medium in the wells was collected and nitrite ions were assayed in the same manner as in Test 1. As a result, significant NO production was observed only from macrophages activated with LPS and administered with the PIC micelles (L-PArg-CS/m, C/A=1) formed with the PEG-b-P(L-Arg) block copolymer synthesized in Example 6 and chondroitin sulfate (FIG. 16). When the PIC micelles (D-PArg-CS/m or L-PLys-Gua/m) formed with the PEG-b-P(D-Arg) block copolymer or the PEG-b-P(L-Lys-Gua) block copolymer synthesized in Example 7 or 8 and chondroitin sulfate were administered, significant NO production was not observed from macrophages activated with LPS. Consequently, it was found that only the PEG-b-P(L-Arg) block copolymer reacts with iNOS enzyme in macrophages to significantly produce NO.

<Test 3>

Evaluation of Antitumor Activity on Tumor-Bearing Mice

Antitumor activity on tumor-bearing mice was evaluated by intravenous administration of PIC micelles (L-PArg-CS/m, C/A=1) formed with the PEG-b-P(L-Arg) block copolymer synthesized in Example 6 and chondroitin sulfate C. The L-PArg-CS/m aqueous solution was prepared according to Example 9. Male Balb/c mice (5-week-old) were grouped (4 animals/group) and reared under the conditions of room temperature 25° C. (±1° C.), 50% humidity and 12 hours light-dark cycle from the receipt of the animals to the end of the present experiment and allowed free access to the feed and water. The mice were inoculated with 100 μL of Colon-26 cancer cells at a cell density of $1\times10^5$ cells/mL on the femur of the right hind limb. The tumor tissue was measured with calipers and indicated as tumor volume (mm³)=[short axis (mm)]²×[long axis (mm)]×0.52. When the average of the tumor volume exceeded 100 mm³, the L-PArg-CS/m aqueous solution was administered as indicated below.

Group 1: single dose of 100 μL saline (PBS);
Group 2: single dose of 100 μL L-PArg-CS/m (arginine concentration: 16 mg/kg);
Group 3: double dose (every other day), in total, of 100 μL L-PArg-CS/m (arginine concentration: 16 mg/kg);
Group 4: triple dose (every other day), in total, of 100 μL L-PArg-CS/m (arginine concentration: 16 mg/kg); and
Group 5: quadruple dose (every other day), in total, of 100 μL L-PArg-CS/m (arginine concentration: 16 mg/kg).

After administration, the tumor volume and the body weight of mice were measured every three days. The change in the relative body weight of mice is shown in FIG. 17. As shown in the figure, no significant body weight reduction was observed for the L-PArg-CS/m (groups 2 to 5) prepared in the present invention compared to the control (group 1), indicating that the PIC micelles do not cause any toxicity. The change in the tumor volume is shown in FIG. 18. In groups 2 and 3, the tumor growth speed is significantly higher than in the control. It is believed that this is because although NO concentration in tumors was increased due to an increased NO production as shown in test 3, the increase of NO concentration was not so high as to exhibit antitumor activity and conversely promoted angiogenesis. In group 4, there is no significant difference compared to the control. In group 5, the tumor growth speed is significantly slowed compared to the control. It is believed that this is because an increased NO production as shown in test 3 induced apoptosis of cancer cells, resulting in suppression of tumor growth.

1. Synthesis of poly(L-Arg)-poly(ethylene glycol)-poly(L-Arg) (PArg-PEG-PArg)

PArg-PEG-PArg was produced by guanidinylation of poly(L-ornithine)-poly(ethylene glycol)-poly(L-ornithine) (POrn-PEG-POrn).

POrn-PEG-POrn was synthesized through ring-opening polymerization of α, ω-NH$_2$ groups of PEG(NH$_2$-PEG-NH$_2$; Mn=10,000) with N-carboxylic acid anhydride of N-δ-carbobenzoxy-L-ornithine (L-Orn(Z)-NCA) followed by elimination of the protecting group.

Example 10

Synthesis of Poly(L-Arg)-b-Poly(Ethylene Glycol)-b-poly(L-Arg) (PArg-b-PEG-b-PArg)

PArg-b-PEG-b-PArg was produced by guanidinylation of poly(L-ornithine)-poly(ethylene glycol)-poly(L-ornithine) (POrn-b-PEG-b-POrn). The symbol "-b-" representing a block copolymer is hereinafter merely abbreviated as "-".

POrn-PEG-Porn was synthesized through ring-opening polymerization of α, ω-NH$_2$ groups of PEG (NH$_2$-PEG-NH$_2$; Mn=10,000) with N-carboxylic acid anhydride of N-δ-carbobenzoxy-L-ornithine (L-Orn(Z)-NCA) followed by elimination of the protecting group.

(1) Synthesis of POrn-PEG-POrn

NH$_2$-PEG-NH$_2$ (2 g, 0.2 mmol) was dissolved in dimethylformamide (DMF, 20 mL) by stirring in a 300-mL round-bottom flask equipped with a 3-way stopcock under a nitrogen atmosphere. In another 100-mL flask, Nδ-benzyloxycarbonyl-L-ornithine acid anhydride (L-Orn(Z)-NCA; 2 g, 6.85 mmol) dissolved in 20 mL DMF was added to the NH$_2$-PEG-NH$_2$ solution by using a N$_2$ purged syringe. The reaction mixture under a dry nitrogen atmosphere was stirred for 48 hours in an oil bath at 30° C. After the reaction, the reaction mixture was precipitated in an ice bath with 15 times excess diethyl ether (600 mL) and filtered. The recovered polymer was reprecipitated twice with diethyl ether to remove impurities. POrn(Z)-PEG-POrn(Z) (2.6 g) was obtained as a white solid. The $^1$H-NMR analysis result of the solid is shown in FIG. 19.

The obtained POrn(Z)-PEG-POrn(Z) (2.6 g) was dissolved in trifluoroacetic acid (TFA, 15 mL) to which hydrobromic acid (HBr, 4.5 mL) was added and stirred in an ice bath for 4 hours. Triethylamine (TEA, 15 mL) was then added dropwise and excess acid was removed. The suspension was then diluted with distilled water (100 mL) and dialyzed against water by using a preliminarily swollen semipermeable tube (MWCO=3500) over 3 days. Dialysis was continued against 0.01 HCl and distilled water to convert TFA-type POrn-PEG-POrn to a HCl-type, followed by lyophilization. POrn-PEG-POrn was obtained as white powder (2.2 g). The $^1$H-NMR analysis result of the white powder is shown in FIG. 19.

(2) Synthesis of PArg-PEG-PArg

PArg-PEG-PArg was obtained by guanidinylation of δ-amino groups in side chains of POrn segments of POrn-PEG-POrn with N,N'-bis(tert-butoxycarbonyl)-1H-pyrazole-1-carboxamidine (PCX(Boc$_2$)) followed by deprotection of Boc groups.

Briefly, POrn-PEG-POrn (1 g, 0.7 mmol) and PCX(Boc$_2$) (1 g, 3.2 mmol) were dissolved in N-methylpyrrolidone (20 mL) containing N,N-diisopropylethylamine (0.5 mL, 3 mmol) and stirred at room temperature for 24 hours. After the reaction, the mixture was precipitated in an ice bath with 15 times excess diethyl ether (300 mL) and filtered. The recovered polymer (PArg(Boc$_2$)-PEG-PArg(Boc$_2$)) was reprecipitated twice with diethyl ether to remove impurities. The polymer (1.1 g) was obtained and the $^1$H-NMR analysis result thereof is shown in FIG. 20. The thus obtained PArg(Boc$_2$)-PEG-PArg(Boc$_2$) was dissolved in TFA (10 mL) and stirred at room temperature for 8 hours. TEA (15 mL) was then added dropwise and excess acid was removed. The suspension was then diluted with distilled water (100 mL), dialyzed against 0.01 HCl and then distilled water and lyophilized. PArg-PEG-PArg (0.9 g) was obtained as white powder. The $^1$H-NMR analysis result of the powder is shown in FIG. 20.

Reference Example

Synthesis of Reactive Oxygen Species (ROS)-Capturing Polymer (PMNT-PEG-PMNT)

Poly(chloromethylstyrene)-polyethylene glycol)-poly(chloromethylstyrene) (PCMS-PEG-PCMS) was synthesized by radical telomerization of chloromethylstyrene using sulfanyl-poly(ethylene glycol)-sulfanyl (HS-PEG-SH; Mn=10,000) as a telogen. Then the chloromethyl groups were converted to TEMPO through interaction of amino groups of 4-amino-2,2,6,6-tetramethylpiperidine 1 oxyl (4-amino-TEMPO) and benzylchloride groups in the PCMS-PEG-PCMS block copolymer. WO2015/118993A may be referred to for specific procedures.

Example 11

Preparation of Polyion Complex (PIC) and Gelation

Polycationic polymers, PArg-PEG-PArg and PMNT-PEG-PMNT, were dissolved in phosphate buffer (pH 6.2, 100 mM). Polyanionic polymers, poly(acrylic acid) (PAAc) and chondroitin sulfate (CS), were also dissolved in phosphate buffer (pH 6.2, 100 mM). To the polycationic polymer solution was added the polyanionic polymer to prepare polyion complex (anion:cation ratio: 1:1). The mixture was stirred at room temperature for 30 minutes and the thus formed PIC micelle particles were analyzed for dynamic light scattering (DLS). The result is shown in table 1 below.

TABLE 1

|  | Average diameter (nm) | Polydispersity index |
| --- | --- | --- |
| PMNT – PEG – PMNT + PAAc | 83 ± 3 | 0.26 ± 0.04 |
| PMNT – PEG – PMNT/ PArg – PEG – PArg + PAAc | 95 ± 9 | 0.24 ± 0.02 |
| PMNT – PEG – PMNT + CS | 64 ± 3 | 0.24 ± 0.02 |
| PMNT – PEG – PMNT/+ PArg – PEG – PArg + CS | 92 ± 4 | 0.25 ± 0.01 |
| PArg – PEG – PArg + CS | 45 ± 3 | 0.15 ± 0.01 |
| PArg – PEG – PArg + PAAc | 58 ± 5 | 0.25 ± 0.03 |

The PIC solution (10 mg/mL) was then concentrated on a centrifugal evaporator until a desired concentration (45 to 60 mg/mL) was attained. Gelation of the thus concentrated PIC under physiological conditions (37° C.) is shown in FIG. 21. From this result, it is found that the PIC micelles efficiently form gel at body temperature.

<Test 4>

Evaluation of Angiogenesis In Vitro

Proangiogenic property of the Arg-PEG-PArg/CS complex was evaluated by human umbilical vein endothelial cell (HUVEC) tube assay using growth-factor-reduced-Matrigel (BD Biosciences).

Briefly, Matrigel was solubilized overnight in cold room temperature (4° C.) according to the manufacturer's protocol. The Matrigel solution (10 μL) was added to a μ-slide (same as above) which was kept in an incubator at 37° C. for 30 minutes to allow polymerization. A HUVEC suspension ($5 \times 10^3$ cells/well) in Dulbecco's modified Eagle's medium (DMEM) was gradually added onto a Matrigel layer in the presence or absence of the Arg-PEG-PArg/CS complex. Vascular endothelial growth factor (VEGF) was used as a positive angiogenesis promoting agent. After incubation under 5% $CO_2$ at 37° C. for 4 hours, DMEM was carefully removed and fresh DMEM containing calcein AM (10 μg/mL) was added onto the Matrigel layer. After incubation for 15 minutes, tube formation was observed under a fluorescence microscope and analyzed by ImageJ software, angiogenesis analyzer plugin. The obtained result showed that PEG-PArg/CS and PArg-PEG-PArg/CS formed tubes in HUVECs. The result is shown in FIG. 22. In the figure, PIC(di) means the PIC derived from the PEG-PArg diblock copolymer prepared according to Example 9 and PIC(tri) means the PIC derived from the PArg-PEG-PArg triblock copolymer.

As indicated in FIG. 22, it is found that PEG-PArg and PArg-PEG-PArg induce tube formation in HUVECs.

<Test 5>

Evaluation of Injectable Hydrogel Based on PMNT-PEG-PMNT/PArg-PEG-PArg in Myocardial Infarction Mice Myocardial infarction (MI) mice were induced by left anterior descending coronary artery (LAD) ligation. Male 7- to 8-week-old ICR mice (body weight: 32 to 35 g) were purchased from Charles River Japan. The mice were reared at a test animal facility of the University of Tsukuba under controlled temperature (23±1° C.), humidity (50±5%) and light/dark (12 hours light-dark cycle). The animals were allowed free access to the feed and water. All experiments were performed pursuant to the regulation of animal tests at the University of Tsukuba. LAD was ligated with an 8-0 silk suture followed by intracardiac injection of the concentrated PIC solution (40 μL, PMNT-PEG-PMNT/PArg-PEG-PArg+ PAAc) at the site of the suture. At 1 week and 4 weeks of post-MI, an echocardiogram test was carried out. The cardiac function was evaluated according to the analysis of the left ventricular ejection fraction and the size of infarction was determined according to the histological evaluation. As shown in FIGS. 23 and 24, mice treated with the injectable gel based on PMNT-PEG-PMNT/PArg-PEG-PArg had significantly improved cardiac function compared to untreated mice. In the figures, Gel 1 indicates the data for PMNT-PEG-PMNT/PArg-PEG-PArg+PAAC (30 mg/mL) and Gel 2 indicates the data for PMNT-PEG-PMNT/PArg-PEG-PArg+ PAAC (60 mg/mL).

With regard to FIG. 24, the heart tissue was fixed in 4% (v/v) buffered formalin for 1 day and in 70% (v/v) alcohol for 2 days and embedded in paraffin. Thin sections with 5 μm thickness of the tissue were then prepared and stained by Masson trichrome staining. The figure shows the results of histological characteristics examination of the thus obtained biological samples under an optical microscope.

INDUSTRIAL APPLICABILITY

The PIC micelles according to the present invention can be used as, for example, a drug for treating tumors without limitation and can be utilized at least in the pharmaceutical industry.

The invention claimed is:

1. A method for producing a block copolymer represented by formula (I):

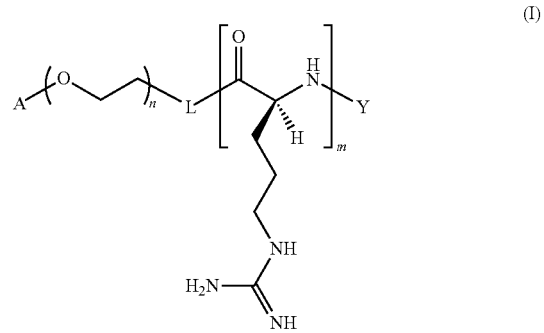

wherein:

A is (i) hydrogen, a $C_1$-$C_{12}$ alkyl group optionally substituted with a formyl group, or a group of the formula $R^1R^2CH$—, wherein $R^1$ and $R^2$ independently represent $C_1$-$C_4$ alkoxy or $R^1$ and $R^2$ together represent —$OCH_2CH_2O$—, —$O(CH_2)_3O$—, or —$O(CH_2)_4O$—, or (ii) a group of the formula:

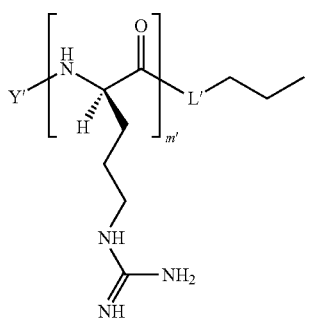

wherein L and L' independently is a linkage group;

Y and Y' independently is H, $C_{1-21}$ alkylcarbonyl, substituted $C_{1-4}$ alkylcarbonyl, optionally substituted $C_{3-7}$ cycloalkylcarbonyl, optionally substituted arylcarbonyl, optionally substituted 5-membered heteroarylcarbonyl, or optionally substituted 6-membered heteroarylcarbonyl, wherein the substituted $C_{1-4}$ alkylcarbonyl is substituted with a substituent selected from the group consisting of a halogen atom, hydroxyl, carboxyl, optionally substituted $C_{3-7}$ cycloalkyl, optionally substituted aryl, optionally substituted 5-membered heteroaryl, optionally substituted 6-membered heteroaryl, optionally substituted adamantyl and a cholesterol residue, wherein the optionally substituted $C_{3-7}$ cycloalkyl, optionally substituted aryl, optionally substituted 5-membered heteroaryl, optionally substituted 6-membered heteroaryl and optionally substituted adamantyl are optionally substituted with a substituent selected from the group consisting of $C_{1-4}$ alkyl, $C_{1-4}$ alkyloxy, hydroxyl, carboxyl, cyano, nitro, a halogen atom mono-$C_{1-4}$ alkylamino and di-$C_{1-4}$ alkylamino, and wherein the cholesterol residue is a cholesterol molecule from which H is eliminated on a carbon at position 22 to 27 or from which a hydrocarbon chain is eliminated;

m and m' are independently an integer of 5 to 300;

n is an integer of 5 to 1,000; and up to 80% of m or m' amidino groups ($C(=NH)NH_2$) are H, the method comprising a step of reacting a block copolymer represented by formula (II):

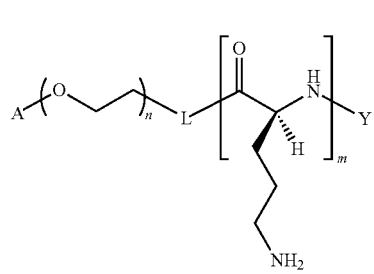

wherein:

A is (i)' (i) as defined for formula (I) above, or (ii)' a group the formula:

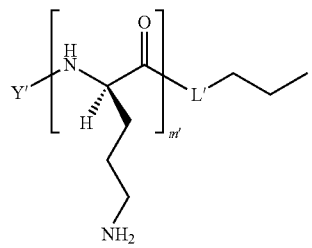

wherein L, L', Y, Y', n, m and m' are as defined for formula (I) above, with N,N'-bis(tert-butoxycarbonyl)-1H-pyrazole-1-carboxamidine optionally in an inert solvent in order to convert a δ-amino group in a segment derived from ornithine to a guanidino group.

2. The method for producing a block copolymer according to claim 1, wherein A in formula (II) is (i)'.

3. The method for producing a block copolymer according to claim 1, wherein A in formula (II) is (ii)'.

* * * * *